US012690787B2

(12) United States Patent
     Goode

(10) Patent No.: US 12,690,787 B2
(45) Date of Patent: Jul. 28, 2026

(54) METHODS AND SYSTEMS FOR CONTINUOUSLY MONITORING THE GLUCOSE LEVEL OF A PATIENT

(71) Applicant: Paul V. Goode, Round Rock, TX (US)

(72) Inventor: Paul V. Goode, Round Rock, TX (US)

(73) Assignee: Glucotrack, Inc., Rutherford, NJ (US)

( * ) Notice: Subject to any disclaimer, the term of this patent is extended or adjusted under 35 U.S.C. 154(b) by 958 days.

(21) Appl. No.: 17/932,238

(22) Filed: Sep. 14, 2022

(65) Prior Publication Data

US 2023/0079720 A1     Mar. 16, 2023

Related U.S. Application Data

(60) Provisional application No. 63/261,164, filed on Sep. 14, 2021.

(51) Int. Cl.
     *A61B 5/1486*     (2006.01)
     *A61B 5/00*       (2006.01)
     (Continued)

(52) U.S. Cl.
     CPC ........ *A61B 5/14865* (2013.01); *A61B 5/0031* (2013.01); *A61B 5/14532* (2013.01);
     (Continued)

(58) Field of Classification Search
     CPC .............. A61B 5/14865; A61B 5/0031; A61B 5/14532; A61B 5/6847; A61B 17/3468; A61B 5/6876
     See application file for complete search history.

(56) References Cited

U.S. PATENT DOCUMENTS 5,395,341 A     3/1995  Slater
6,558,351 B1    5/2003  Steil
        (Continued)

FOREIGN PATENT DOCUMENTS

CN     100546535 C    10/2009
CN     102858242 B     5/2014
        (Continued)

OTHER PUBLICATIONS

International Search Report for PCT/US22/76435, Jan. 30, 2023.
        (Continued)

*Primary Examiner* — Christian Jang
(74) *Attorney, Agent, or Firm* — Novel IP

(57)          ABSTRACT

A device for continuously monitoring glucose levels in a patient is disclosed. The device includes a glucose electronics assembly and a glucose lead assembly in electrical communication with the glucose electronics assembly. The glucose electronics assembly is configured to be positioned in the subcutaneous tissue and the glucose lead assembly is configured to be positioned in a vessel of the patient. The glucose lead assembly has a central shaft, a first electrode in physical communication with the central shaft, a second electrode in physical communication with the central shaft, a third electrode in physical communication with the central shaft and a positioning element configured to have an undeployed state and a deployed state. In the undeployed state, the positioning element is substantially linear, and in the deployed state, the positioning element extends away from the central shaft.

21 Claims, 12 Drawing Sheets

(51) Int. Cl.

| | |
|---|---|
| *A61B 5/145* | (2006.01) |
| *A61B 17/32* | (2006.01) |
| *A61B 17/34* | (2006.01) |

(52) U.S. Cl.

CPC ........ *A61B 5/6847* (2013.01); *A61B 17/3468* (2013.01); *A61B 5/6876* (2013.01); *A61B 2017/320056* (2013.01); *A61B 2562/04* (2013.01)

(56) References Cited

U.S. PATENT DOCUMENTS

| | | | |
|---|---|---|---|
| 6,702,857 | B2 | 3/2004 | Brauker |
| 6,862,465 | B2 | 3/2005 | Shults |
| 6,931,327 | B2 | 8/2005 | Goode, Jr. |
| 6,954,662 | B2 | 10/2005 | Freger |
| 7,108,778 | B2 | 9/2006 | Simpson |
| 7,134,999 | B2 | 11/2006 | Brauker |
| 7,136,689 | B2 | 11/2006 | Shults |
| 7,192,450 | B2 | 3/2007 | Brauker |
| 7,226,978 | B2 | 6/2007 | Tapsak |
| 7,276,029 | B2 | 10/2007 | Goode, Jr. |
| 7,366,556 | B2 | 4/2008 | Brister |
| 7,379,765 | B2 | 5/2008 | Petisce |
| 7,424,318 | B2 | 9/2008 | Brister |
| 7,460,898 | B2 * | 12/2008 | Brister ............... A61B 5/14532 |
| | | | 600/347 |
| 7,471,972 | B2 | 12/2008 | Rhodes |
| 7,583,990 | B2 | 9/2009 | Goode, Jr. |
| 7,591,801 | B2 | 9/2009 | Brauker |
| 7,599,726 | B2 | 10/2009 | Goode, Jr. |
| 7,615,007 | B2 | 11/2009 | Shults |
| 7,632,228 | B2 | 12/2009 | Brauker |
| 7,657,297 | B2 | 2/2010 | Simpson |
| 7,715,893 | B2 | 5/2010 | Kamath |
| 7,761,130 | B2 | 7/2010 | Simpson |
| 7,778,680 | B2 | 8/2010 | Goode, Jr. |
| 7,797,028 | B2 | 9/2010 | Goode, Jr. |
| 7,811,763 | B2 | 10/2010 | Poli |
| 7,826,981 | B2 | 11/2010 | Goode, Jr. |
| 7,828,728 | B2 | 11/2010 | Boock |
| 7,860,545 | B2 | 12/2010 | Shults |
| 7,885,697 | B2 | 2/2011 | Brister |
| 7,896,809 | B2 | 3/2011 | Simpson |
| 7,914,450 | B2 | 3/2011 | Goode, Jr. |
| 7,917,186 | B2 | 3/2011 | Kamath |
| 7,920,906 | B2 | 4/2011 | Goode, Jr. |
| 7,925,321 | B2 | 4/2011 | Goode, Jr. |
| 7,933,639 | B2 | 4/2011 | Goode, Jr. |
| 7,935,057 | B2 | 5/2011 | Goode, Jr. |
| 7,955,261 | B2 | 6/2011 | Goode |
| 7,959,569 | B2 | 6/2011 | Goode |
| 7,976,492 | B2 | 7/2011 | Brauker |
| 7,979,104 | B2 | 7/2011 | Kamath |
| 7,986,986 | B2 | 7/2011 | Goode |
| 7,998,071 | B2 | 8/2011 | Goode, Jr. |
| 8,005,525 | B2 | 8/2011 | Goode, Jr. |
| 8,010,174 | B2 | 8/2011 | Goode, Jr. |
| 8,050,731 | B2 | 11/2011 | Tapsak |
| 8,052,601 | B2 | 11/2011 | Goode, Jr. |
| 8,053,018 | B2 | 11/2011 | Tapsak |
| 8,060,173 | B2 | 11/2011 | Goode, Jr. |
| RE43,039 | E | 12/2011 | Brister |
| 8,073,519 | B2 | 12/2011 | Goode, Jr. |
| 8,073,520 | B2 | 12/2011 | Kamath |
| 8,086,323 | B2 | 12/2011 | Reghabi |
| 8,118,877 | B2 | 2/2012 | Brauker |
| 8,128,562 | B2 | 3/2012 | Goode, Jr. |
| 8,150,488 | B2 | 4/2012 | Goode, Jr. |
| 8,155,723 | B2 | 4/2012 | Shults |
| 8,160,671 | B2 | 4/2012 | Kamath |
| RE43,399 | E | 5/2012 | Simpson |
| 8,167,801 | B2 | 5/2012 | Goode, Jr. |
| 8,195,265 | B2 | 6/2012 | Goode, Jr. |
| 8,206,297 | B2 | 6/2012 | Kamath |

| | | | |
|---|---|---|---|
| 8,229,536 | B2 | 7/2012 | Goode, Jr. |
| 8,235,897 | B2 | 8/2012 | Gal |
| 8,249,684 | B2 | 8/2012 | Kamath |
| 8,255,030 | B2 | 8/2012 | Petisce |
| 8,255,032 | B2 | 8/2012 | Petisce |
| 8,255,033 | B2 | 8/2012 | Petisce |
| 8,277,713 | B2 | 10/2012 | Petisce |
| 8,285,354 | B2 | 10/2012 | Goode |
| 8,290,562 | B2 | 10/2012 | Goode, Jr. |
| 8,292,810 | B2 | 10/2012 | Goode, Jr. |
| 8,298,142 | B2 | 10/2012 | Simpson |
| 8,332,008 | B2 | 12/2012 | Goode |
| 8,346,338 | B2 | 1/2013 | Goode, Jr. |
| 8,364,229 | B2 | 1/2013 | Simpson |
| 8,364,230 | B2 | 1/2013 | Simpson |
| 8,364,231 | B2 | 1/2013 | Kamath |
| 8,386,004 | B2 | 2/2013 | Kamath |
| 8,396,528 | B2 | 3/2013 | Kamath |
| 8,412,301 | B2 | 4/2013 | Goode, Jr. |
| 8,425,416 | B2 | 4/2013 | Brister |
| 8,428,678 | B2 | 4/2013 | Kamath |
| 8,428,679 | B2 | 4/2013 | Goode, Jr. |
| 8,435,179 | B2 | 5/2013 | Goode, Jr. |
| 8,442,610 | B2 | 5/2013 | Goode |
| 8,444,560 | B2 | 5/2013 | Hayter |
| 8,449,464 | B2 | 5/2013 | Simpson |
| 8,460,231 | B2 | 6/2013 | Brauker |
| 8,483,793 | B2 | 7/2013 | Simpson |
| 8,491,474 | B2 | 7/2013 | Goode, Jr. |
| 8,509,871 | B2 | 8/2013 | Rhodes |
| 8,527,026 | B2 | 9/2013 | Shults |
| 8,532,730 | B2 | 9/2013 | Brister |
| 8,540,648 | B2 | 9/2013 | Uihlein |
| 8,548,551 | B2 | 10/2013 | Kamath |
| 8,548,553 | B2 | 10/2013 | Kamath |
| 8,560,037 | B2 | 10/2013 | Goode, Jr. |
| 8,560,038 | B2 | 10/2013 | Hayter |
| 8,560,039 | B2 | 10/2013 | Simpson |
| 8,565,849 | B2 | 10/2013 | Kamath |
| 8,565,867 | B2 | 10/2013 | Armstrong |
| 8,571,625 | B2 | 10/2013 | Kamath |
| 8,579,816 | B2 | 11/2013 | Kamath |
| 8,588,882 | B2 | 11/2013 | Kamath |
| 8,600,681 | B2 | 12/2013 | Hayter |
| 8,622,905 | B2 | 1/2014 | Kamath |
| 8,657,747 | B2 | 2/2014 | Kamath |
| 8,672,845 | B2 | 3/2014 | Kamath |
| 8,676,287 | B2 | 3/2014 | Kamath |
| 8,721,585 | B2 | 5/2014 | Brauker |
| 8,761,856 | B2 | 6/2014 | Goode, Jr. |
| 8,771,187 | B2 | 7/2014 | Goode, Jr. |
| 8,774,888 | B2 | 7/2014 | Kamath |
| 8,788,006 | B2 | 7/2014 | Kamath |
| 8,788,008 | B2 | 7/2014 | Goode, Jr. |
| 8,790,260 | B2 | 7/2014 | Goode, Jr. |
| 8,792,955 | B2 | 7/2014 | Brister |
| 8,795,177 | B2 | 8/2014 | Goode, Jr. |
| 8,801,612 | B2 | 8/2014 | Goode |
| 8,808,182 | B2 | 8/2014 | Goode, Jr. |
| 8,812,073 | B2 | 8/2014 | Goode, Jr. |
| 8,821,400 | B2 | 9/2014 | Goode, Jr. |
| 8,840,552 | B2 | 9/2014 | Brauker |
| 8,843,187 | B2 | 9/2014 | Goode, Jr. |
| 8,862,197 | B2 | 10/2014 | Kamath |
| 8,865,249 | B2 | 10/2014 | Tapsak |
| 8,880,371 | B2 | 11/2014 | Beyer |
| 8,882,741 | B2 | 11/2014 | Brauker |
| 8,909,314 | B2 | 12/2014 | Petisce |
| 8,909,339 | B2 | 12/2014 | Win |
| 8,911,367 | B2 | 12/2014 | Brister |
| 8,911,369 | B2 | 12/2014 | Brister |
| 8,920,401 | B2 | 12/2014 | Brauker |
| 8,923,947 | B2 | 12/2014 | Shults |
| 8,926,585 | B2 | 1/2015 | Brauker |
| 8,929,968 | B2 | 1/2015 | Brister |
| 8,934,975 | B2 | 1/2015 | Yaniv |
| 8,948,836 | B2 | 2/2015 | Reghabi |
| 8,954,128 | B2 | 2/2015 | Boock |
| 9,037,210 | B2 | 5/2015 | Simpson |

(56) References Cited

U.S. PATENT DOCUMENTS

| | | | |
|---|---|---|---|
| 9,050,413 B2 | 6/2015 | Brauker | |
| 9,149,219 B2 | 10/2015 | Goode, Jr. | |
| 9,155,843 B2 | 10/2015 | Brauker | |
| 9,179,869 B2 | 11/2015 | Tapsak | |
| 9,220,449 B2 | 12/2015 | Pryor | |
| 9,237,864 B2 | 1/2016 | Simpson | |
| 9,328,371 B2 | 5/2016 | Rhodes | |
| 9,339,222 B2 | 5/2016 | Simpson | |
| 9,427,183 B2 | 8/2016 | Goode, Jr. | |
| 9,439,589 B2 | 9/2016 | Shults | |
| 9,451,908 B2 | 9/2016 | Kamath | |
| 9,451,910 B2 | 9/2016 | Brister | |
| 9,498,155 B2 | 11/2016 | Brauker | |
| 9,532,741 B2 | 1/2017 | Brauker | |
| 9,549,699 B2 | 1/2017 | Boock | |
| 9,566,026 B2 | 2/2017 | Boock | |
| 9,572,523 B2 | 2/2017 | Boock | |
| 9,597,027 B2 | 3/2017 | Petisce | |
| 9,668,682 B2 | 6/2017 | Brister | |
| 9,693,688 B2 | 7/2017 | Sicurello | |
| 9,713,446 B2 | 7/2017 | Gal | |
| 9,724,045 B1 | 8/2017 | Goode, Jr. | |
| 9,737,250 B2 | 8/2017 | Hughes | |
| 9,750,441 B2 | 9/2017 | Brauker | |
| 9,801,574 B2 | 10/2017 | Tapsak | |
| 9,804,114 B2 | 10/2017 | Rhodes | |
| 9,833,143 B2 | 12/2017 | Brister | |
| 9,848,805 B2 | 12/2017 | Dang | |
| 9,872,985 B2 | 1/2018 | Butera | |
| 9,895,089 B2 | 2/2018 | Goode, Jr. | |
| 9,918,668 B2 | 3/2018 | Pryor | |
| 9,931,067 B2 | 4/2018 | Shults | |
| 9,937,293 B2 | 4/2018 | Brauker | |
| 9,949,639 B2 | 4/2018 | Sicurello | |
| 9,993,186 B2 | 6/2018 | Petisce | |
| 10,028,683 B2 | 7/2018 | Simpson | |
| 10,028,684 B2 | 7/2018 | Simpson | |
| 10,039,480 B2 | 8/2018 | Brauker | |
| 10,154,807 B2 | 12/2018 | Tapsak | |
| 10,188,333 B2 | 1/2019 | Kamath | |
| 10,194,850 B2 | 2/2019 | Kovatchev | |
| 10,238,339 B2 | 3/2019 | Dlugach | |
| 10,327,638 B2 | 6/2019 | Brister | |
| 10,349,873 B2 | 7/2019 | Kamath | |
| 10,376,143 B2 | 8/2019 | Simpson | |
| 10,383,575 B2 | 8/2019 | Najafi | |
| 10,420,494 B2 | 9/2019 | Simpson | |
| 10,561,352 B2 | 2/2020 | Simpson | |
| 10,602,968 B2 | 3/2020 | Kamath | |
| 10,610,102 B2 | 4/2020 | Brister | |
| 10,610,103 B2 | 4/2020 | Brister | |
| 10,610,135 B2 | 4/2020 | Kamath | |
| 10,610,136 B2 | 4/2020 | Kamath | |
| 10,610,137 B2 | 4/2020 | Kamath | |
| 10,610,140 B2 | 4/2020 | Petisce | |
| 10,617,336 B2 | 4/2020 | Kamath | |
| 10,624,539 B2 | 4/2020 | Brister | |
| 10,638,962 B2 | 5/2020 | Lucisano | |
| 10,674,937 B2 | 6/2020 | Colvin, Jr. | |
| 10,709,332 B2 | 7/2020 | Brister | |
| 10,709,362 B2 | 7/2020 | Simpson | |
| 10,709,364 B2 | 7/2020 | Kamath | |
| 10,716,498 B2 | 7/2020 | Kamath | |
| 10,743,801 B2 | 8/2020 | Kamath | |
| 10,786,185 B2 | 9/2020 | Goode, Jr. | |
| 10,827,956 B2 | 11/2020 | Brister | |
| 10,835,130 B2 | 11/2020 | Cho | |
| 10,856,787 B2 | 12/2020 | Pryor | |
| 10,898,113 B2 | 1/2021 | Brauker | |
| 10,898,114 B2 | 1/2021 | Kamath | |
| 10,908,114 B2 | 2/2021 | Estes | |
| 10,918,313 B2 | 2/2021 | Brister | |
| 10,918,314 B2 | 2/2021 | Brister | |
| 10,918,315 B2 | 2/2021 | Brister | |
| 10,918,316 B2 | 2/2021 | Pryor | |
| 10,918,317 B2 | 2/2021 | Pryor | |
| 10,918,318 B2 | 2/2021 | Pryor | |
| 10,925,524 B2 | 2/2021 | Pryor | |
| 10,932,700 B2 | 3/2021 | Simpson | |
| 10,980,452 B2 | 4/2021 | Simpson | |
| 10,993,641 B2 | 5/2021 | Brister | |
| 10,993,642 B2 | 5/2021 | Simpson | |
| 11,000,213 B2 | 5/2021 | Kamath | |
| 11,026,605 B1 | 6/2021 | Simpson | |
| 11,045,120 B2 | 6/2021 | Simpson | |
| 11,051,726 B2 | 7/2021 | Kamath | |
| 11,064,917 B2 | 7/2021 | Simpson | |
| 11,160,506 B2 | 11/2021 | Dlugach | |
| 11,246,990 B2 | 2/2022 | Brauker | |
| 11,247,057 B1 | 2/2022 | Gliner | |
| 11,284,816 B2 | 3/2022 | Shah | |
| 11,399,745 B2 | 8/2022 | Simpson | |
| 11,534,611 B2 | 12/2022 | Baldoni | |
| 11,633,133 B2 | 4/2023 | Brister | |
| 11,638,541 B2 | 5/2023 | Brauker | |
| 11,672,422 B2 | 6/2023 | Brister | |
| 11,883,164 B2 | 1/2024 | Kamath | |
| 11,892,426 B2 | 2/2024 | Estes | |
| 11,896,374 B2 | 2/2024 | Kamath | |
| 11,918,354 B2 | 3/2024 | Simpson | |
| 11,923,063 B2 | 3/2024 | Georgiou | |
| 12,016,648 B2 | 6/2024 | Brister | |
| 12,115,357 B2 | 10/2024 | Brauker | |
| 12,226,617 B2 | 2/2025 | Brauker | |
| 2002/0042630 A1 | 4/2002 | Bardy | |
| 2003/0032874 A1 | 2/2003 | Rhodes | |
| 2005/0090607 A1 | 4/2005 | Tapsak | |
| 2005/0245799 A1 | 11/2005 | Brauker | |
| 2006/0015020 A1 | 1/2006 | Neale | |
| 2006/0058854 A1 | 3/2006 | Abrams | |
| 2006/0068208 A1 | 3/2006 | Tapsak | |
| 2006/0258761 A1 | 11/2006 | Boock | |
| 2007/0032718 A1 | 2/2007 | Shults | |
| 2007/0213611 A1 | 9/2007 | Simpson | |
| 2007/0299617 A1 | 12/2007 | Willis | |
| 2008/0033260 A1 | 2/2008 | Sheppard | |
| 2008/0045824 A1 | 2/2008 | Tapsak | |
| 2008/0119703 A1* | 5/2008 | Brister | A61B 5/14532 |
| | | | 600/347 |
| 2008/0228054 A1 | 9/2008 | Shults | |
| 2009/0062633 A1 | 3/2009 | Brauker | |
| 2010/0036225 A1 | 2/2010 | Goode, Jr. | |
| 2010/0041971 A1 | 2/2010 | Goode, Jr. | |
| 2010/0168542 A1 | 7/2010 | Kamath | |
| 2010/0168543 A1 | 7/2010 | Kamath | |
| 2010/0168657 A1 | 7/2010 | Kamath | |
| 2010/0185071 A1 | 7/2010 | Simpson | |
| 2010/0198035 A1 | 8/2010 | Kamath | |
| 2010/0198036 A1 | 8/2010 | Kamath | |
| 2010/0286496 A1 | 11/2010 | Simpson | |
| 2011/0077490 A1 | 3/2011 | Simpson | |
| 2011/0124992 A1 | 5/2011 | Brauker | |
| 2011/0231140 A1 | 9/2011 | Goode, Jr. | |
| 2011/0313543 A1 | 12/2011 | Brauker | |
| 2012/0040101 A1 | 2/2012 | Tapsak | |
| 2012/0190953 A1 | 7/2012 | Brauker | |
| 2012/0258162 A1 | 10/2012 | Tapsak | |
| 2012/0271133 A1 | 10/2012 | Gal | |
| 2012/0283537 A1 | 11/2012 | Petisce | |
| 2013/0237786 A1 | 9/2013 | Goode, Jr. | |
| 2014/0088389 A1 | 3/2014 | Simpson | |
| 2015/0219129 A1 | 8/2015 | Gal | |
| 2016/0235348 A1 | 8/2016 | Kamath | |
| 2016/0354018 A1 | 12/2016 | Brauker | |
| 2017/0188923 A1 | 7/2017 | Zou | |
| 2017/0191955 A1 | 7/2017 | Zou | |
| 2017/0215777 A1 | 8/2017 | Brauker | |
| 2017/0231497 A1 | 8/2017 | Brister | |
| 2018/0024086 A1 | 1/2018 | Rhodes | |
| 2018/0055423 A1 | 3/2018 | Pryor | |
| 2018/0160949 A1 | 6/2018 | Brister | |
| 2018/0192926 A1 | 7/2018 | Shults | |
| 2018/0199873 A1 | 7/2018 | Wang | |
| 2018/0317827 A1 | 11/2018 | Brauker | |

(56) References Cited

U.S. PATENT DOCUMENTS

| | | | |
|---|---|---|---|
| 2019/0021596 | A1 | 1/2019 | Brister |
| 2019/0069817 | A1 | 3/2019 | Brister |
| 2019/0083018 | A1 | 3/2019 | Tapsak |
| 2019/0110724 | A1 | 4/2019 | Kamath |
| 2019/0239782 | A1 | 8/2019 | Shults |
| 2019/0320955 | A1 | 10/2019 | Pryor |
| 2019/0320956 | A1 | 10/2019 | Pryor |
| 2019/0320957 | A1 | 10/2019 | Pryor |
| 2019/0343436 | A1 | 11/2019 | Pryor |
| 2020/0155049 | A1 | 5/2020 | Pryor |
| 2020/0155050 | A1 | 5/2020 | Pryor |
| 2020/0187834 | A1 | 6/2020 | Petisce |
| 2020/0352482 | A1 | 11/2020 | Gal |
| 2020/0359945 | A1 | 11/2020 | Kamath |
| 2020/0359946 | A1 | 11/2020 | Kamath |
| 2020/0359947 | A1 | 11/2020 | Kamath |
| 2020/0405202 | A1 | 12/2020 | Goode, Jr. |
| 2021/0038136 | A1 | 2/2021 | Kamath |
| 2021/0045663 | A1 | 2/2021 | Simpson |
| 2021/0045665 | A1 | 2/2021 | Simpson |
| 2021/0045666 | A1 | 2/2021 | Simpson |
| 2021/0045667 | A1 | 2/2021 | Kamath |
| 2021/0045669 | A1 | 2/2021 | Kamath |
| 2021/0045670 | A1 | 2/2021 | Kamath |
| 2021/0100452 | A1 | 4/2021 | Brister |
| 2021/0145333 | A1 | 5/2021 | Kamath |
| 2021/0186381 | A1 | 6/2021 | Brister |
| 2021/0251532 | A1 | 8/2021 | Simpson |
| 2021/0251533 | A1 | 8/2021 | Simpson |
| 2021/0267509 | A1 | 9/2021 | Kamath |
| 2021/0290119 | A1 | 9/2021 | Simpson |
| 2021/0321914 | A1 | 10/2021 | Brister |
| 2021/0369114 | A1 | 12/2021 | Brister |
| 2022/0054055 | A1 | 2/2022 | Simpson |
| 2022/0054056 | A1 | 2/2022 | Simpson |
| 2022/0125357 | A1 | 4/2022 | Kamath |
| 2022/0202322 | A1 | 6/2022 | Clary |
| 2022/0214300 | A1 | 7/2022 | Wang |
| 2023/0138407 | A1 | 5/2023 | Zou |
| 2023/0139158 | A1 | 5/2023 | Zou |
| 2023/0200691 | A1 | 6/2023 | Brister |
| 2024/0049997 | A1 | 2/2024 | Brister |
| 2024/0057865 | A1 | 2/2024 | Brister |
| 2024/0324877 | A1 | 10/2024 | Brister |
| 2024/0382093 | A1 | 11/2024 | Brister |
| 2025/0032006 | A1 | 1/2025 | Brister |

FOREIGN PATENT DOCUMENTS

| | | | |
|---|---|---|---|
| CN | 104116512 | B | 5/2017 |
| CN | 107252307 | B | 3/2021 |
| EP | 1656065 | B1 | 7/2011 |
| EP | 2425770 | A | 3/2012 |
| EP | 2129285 | B1 | 7/2014 |
| EP | 2563222 | B1 | 12/2014 |
| EP | 2967345 | B1 | 3/2017 |
| EP | 2767234 | B1 | 1/2019 |
| EP | 3485812 | B1 | 6/2021 |
| WO | 2005017642 | A2 | 2/2005 |
| WO | 2011135562 | A2 | 11/2011 |
| WO | 2014141236 | A1 | 9/2014 |

OTHER PUBLICATIONS

Written Opinion of the International Searching Authority for PCT/US22/76435, Jan. 30, 2023.
Central Venous Catheterization and Central Venous Pressure Monitoring. Roberts and Hedges' Clinical Procedures in Emergency Medicine and Acute Care [online]. 7th edition. Philadelphia, PA: Elsevier, 2019 [retrieved on Dec. 28, 2022]. Retrieved from the Internet: <URL:https://www.sciencedirect.com/topics/medicine-and-dentitstry/seldinger-technique>.
International Search Report for PCT/US25/24342, Jun. 16, 2025.
Written Opinion of the International Searching Authority for PCT/US25/24342, Jun. 16, 2025.
T.-H. Chou, S. Yu, S. Bose, J. Cook, J. Park and M. L. Johnston, "Wireless, Multi-Sensor System-on-Chip for pH and Amperometry Powered by Body Heat," in IEEE Transactions on Biomedical Circuits and Systems, vol. 17, No. 4, pp. 782-794, Aug. 2023 (Year: 2023).

* cited by examiner

202: Subclavian Vein

206: Vessel Insertion Point

200: Glucose Sensor Lead Assembly

220: Glucose Sensor Electronics Assembly

204: Superior Vena Cava

210b — Insert dilator catheter into subclavian vein over guidewire

212b — Remove guidewire

214b — Insert lead assembly in electrical communication with electronics assembly 202b — Insert needle using syringe into subclavian vein 204b — Disconnect needle from syringe 206b — Insert guidewire through needle lumen 208b — Remove needle 550: Catheter 510: Glucose Sensor
Lead Assembly

580

540: Nitinol Wire
inside Catheter

560

570

500

800

872

871: Spiral Nitinol
Wire inside Vessel

860: Vessel

812

810: Glucose
Sensor Lead Assembly

870: Spiral Nitinol Wire inside Vesse

1160: Vessel

1171: Three-Pronged Nitinol Wire
inside Vessel (third prong not shown)

1112

1110: Glucose Sensor Lead Assembly

1100

METHODS AND SYSTEMS FOR CONTINUOUSLY MONITORING THE GLUCOSE LEVEL OF A PATIENT

CROSS-REFERENCE

The present application relies on, for priority, U.S. Patent Provisional Application No. 63/261,164, entitled "Methods and Systems for Continuously Monitoring the Glucose Level of a Patient" and filed on Sep. 14, 2021, which is herein incorporated by reference in its entirety.

FIELD

Embodiments of the present specification relate to the field of monitoring glucose levels in a patient. Specifically, the embodiments relate to devices and treatment protocols for continuously monitoring the glucose level of a patient in a manner that is reliable and robust.

BACKGROUND

There are many different types of glucose sensors for continuous monitoring of glucose levels. Implantable glucose sensors may be subcutaneous or intravascular. Percutaneous glucose sensors may also be subcutaneous or intravascular. Glucose monitoring maybe effectuated using a variety of different sensing modalities, including enzymatic, fluorescence sensing, and optical sensing.

Percutaneous and implantable continuous glucose sensors require sensing elements with a small surface area and volume to prevent insertion pain and wearer discomfort. Smaller size of implantable subcutaneous sensors is especially important because the larger sensor mass and volume not only creates discomfort for the user, but also exacerbates a subcutaneous foreign body response. An increased foreign body response decreases the chances of proper wound healing and of neovascularization, which are necessary to support proper and sufficient diffusion of glucose and oxygen into the sensing element. Conventional implantable intravascular sensors are also limited in size since their sensing elements and some of the supporting electronics are designed to fit within a diameter of a blood vessel without occluding blood flow.

One of the limitations of reducing the surface area and volume of any glucose sensor is the consequent limit to an amount of a glucose sensing agent that can be incorporated over the sensing element. Examples of sensing agents include glucose oxidase and boronic acid, among other types of agents. The limited ability to incorporate sensing agents over reduced size and volume of a glucose sensing element is further worsened by the degradation of some types of agents over time. As a result of continually degrading presence of the limited amount of a glucose sensing agent, determined by the limited surface area and volume of the sensing element, a sensor output (in the form of a measured current from one or more sensing electrodes) continuously diminishes for a specific amount of glucose concentration. For subcutaneously implanted glucose sensors, the glucose sensing agent degradation problem is further exacerbated by the inflammatory response of macrophages, foreign body giant cells, and fibroblasts, among other bodily elements, which occurs post device implant, as well as a result of any minor physical trauma or injury to the site. The mentioned problems change and/or diminish sensor-tissue interface integrity over time.

Conventional glucose sensors have attempted to overcome these problems by increasing the presence of glucose sensing agents on the sensing elements, resulting in extended life of the sensing agent and the corresponding sensor function. Moreover, sensors using glucose oxidase as the sensing agent, limited further the amount of glucose diffusion to reduce the number of oxidation/reduction cycles while also relatively increasing the enzyme concentration. As such, percutaneous sensors which initially lasted for 2-3 days are now lasting 10-14 days before sensor output becomes inaccurate. However, the diffusion rate can only be decreased to a certain level before sensor measurements (current levels) approach a minimum acceptable signal-to-noise ratio, and clinically relevant diffusion delays occur. This problem may be overcome by increasing the surface area of the sensing element to increase the sensor current level. However, the need to limit the sensor size and volume is important and may otherwise introduce pain and/or discomfort to the user. Additionally, the conventional sensors could not substantially increase membrane thickness to accommodate more glucose oxidase because the resulting increase would lead to diffusion delays resulting in a clinically unacceptable lag time in measured glucose.

Therefore, there is a need for systems and methods for continuously monitoring glucose that overcome the surface area and volume constraints of sensor elements, the problem of glucose sensing agent depletion, and poor signal to noise ratios, as discussed above.

SUMMARY

The following embodiments and aspects thereof are described and illustrated in conjunction with systems, tools and methods, which are meant to be exemplary and illustrative, and not limiting in scope. The present application discloses numerous embodiments.

The present specification discloses a device for continuously monitoring glucose levels in a patient, comprising: a glucose electronics assembly; and a glucose lead assembly in electrical communication with the glucose electronics assembly, wherein the glucose electronics assembly is configured to be positioned in the subcutaneous tissue and the glucose lead assembly is configured to be positioned in a vessel of the patient and wherein the glucose lead assembly comprises a central shaft, a first electrode in physical communication with the central shaft, a second electrode in physical communication with the central shaft, and at least one positioning element configured to have an undeployed state and a deployed state, wherein, in the undeployed state, the positioning element is substantially linear, and in the deployed state, the positioning element extends away from the central shaft.

Optionally, the glucose lead assembly comprises a third electrode in physical communication with the central shaft.

Optionally, in the deployed state, the positioning element is defined by at least one curved member. Optionally, a length extending from one end of the at least one curved member to an opposing end of the curved member is at least 10% less than the diameter of the vessel.

Optionally, in the deployed state, the positioning element is defined by at least two or more prongs having a distal end extending away from the central shaft, wherein each prong is equally spaced radially around the central shaft, and wherein each prong extends away from the remaining of the at least two or more prongs and from the central shaft.

Optionally, the at least one positioning element is made from a shape-memory element. Optionally, the shape-memory element is Nitinol.

Optionally, the glucose lead assembly is positioned in the vessel of one of a central venous vasculature, a peripheral venous vasculature, or a spinal column.

Optionally, at least one of the first electrode, the second electrode, or the third electrode form a sensor for continuously monitoring glucose levels in the patient, wherein the sensor is at least one of an enzymatic sensor or a non-enzymatic sensor. Optionally, the enzymatic sensor comprises at least one of a wired enzymatic sensor, an engineered enzymatic sensor, an $H_2O_2$ based enzymatic sensor, or an $O_2$ differential based enzymatic sensor. Optionally, the non-enzymatic sensor comprises at least one of a photodetector or a glucose binding molecule.

Optionally, a structure of at least one of the first electrode, the second electrode, or the third electrode is at least one of a coil, a ring, or a paddle.

Optionally, at least one of the first electrode, the second electrode, or the third electrode comprises more than one electrode that are electrically connected to each other.

Optionally, at least one of the first electrode, the second electrode, or the third electrode comprises one or more bioresorbable membranes.

Optionally, at least one of the first electrode, the second electrode, or the third electrode comprises at least one of platinum, silver-silver chloride, or iridium oxide.

Optionally, the glucose electronics assembly comprises at least one of a potentiostat, an analog to digital converter, a power source, a digital communication circuit, or a microcontroller. Optionally, one or more of the potentiostat, the analog to digital converter, the power source, the digital communication circuit, or the microcontroller are integrated within the glucose lead assembly.

Optionally, the glucose electronics assembly is configured to interface wirelessly with an external computing device.

The present specification also discloses a method for continuously monitoring glucose levels in a patient, comprising: inserting a needle using a syringe, into a blood vessel of the patient; disconnecting the needle from the syringe; inserting a guide wire through a lumen of the needle; removing the needle; inserting a dilator catheter into the blood vessel over the guide wire; removing the guide wire; inserting a glucose lead assembly through the dilator catheter into the blood vessel, wherein the glucose lead assembly is in electrical communication on a proximal side with a glucose electronics assembly, wherein the glucose lead assembly is configured to be positioned in the blood vessel of the patient and wherein the glucose lead assembly comprises a central shaft, a first electrode in physical communication with the central shaft, a second electrode in physical communication with the central shaft, and at least one positioning element configured to have an undeployed state and a deployed state, wherein, in the undeployed state, the positioning element is substantially linear, and in the deployed state, the positioning element extends away from the central shaft; wherein a proximal portion of the glucose electronics assembly is positioned outside the patient.

Optionally, the blood vessel is a subclavian vein and the inserting the needle comprises inserting the needle to a position that is at a top level of a manubrium and about two-thirds distal of the manubrium just beyond a clavicle of the patient.

Optionally, the inserting the dilator catheter further comprises making an incision at a site of the inserting.

Optionally, the inserting the glucose assembly comprises inserting to a depth, wherein the depth is determined with one or more marks on at least one of the guidewire, the dilator catheter, or the glucose lead assembly.

Optionally, the inserting comprises using a tunneling tube up to a depth of 2 centimeters to create a subcutaneous pocket for the glucose electronics assembly.

Optionally, the method further comprises maintaining the glucose lead assembly in the blood vessel for a minimum period of 24 months.

Optionally, the method further comprises replacing the glucose lead assembly in the blood vessel for a minimum period of 24 months.

Optionally, the blood vessel is a subclavian vein.

The aforementioned and other embodiments of the present specification shall be described in greater depth in the drawings and detailed description provided below.

BRIEF DESCRIPTION OF THE DRAWINGS

The accompanying drawings illustrate various embodiments of systems, methods, and embodiments of various other aspects of the disclosure. Any person with ordinary skills in the art will appreciate that the illustrated element boundaries (e.g. boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another and vice versa. Furthermore, elements may not be drawn to scale. Non-limiting and non-exhaustive descriptions are described with reference to the following drawings. The components in the figures are not necessarily to scale, emphasis instead being placed upon illustrating principles.

DETAILED DESCRIPTION

Figure 1:
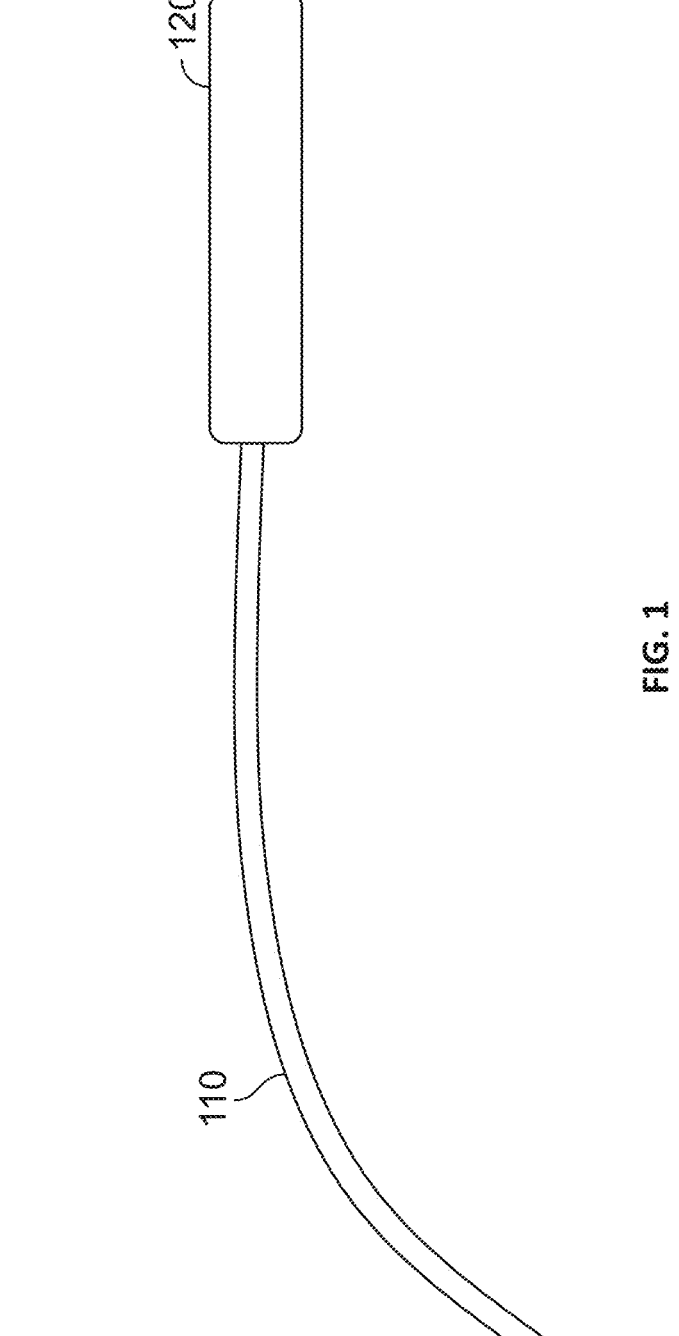
FIG. 1 illustrates an exemplary layout of a continuous glucose sensor comprising a glucose sensor lead assembly and a hermetically sealed glucose sensor electronics assembly, in accordance with some embodiments of the present specification.

The present specification is directed towards systems and methods for continuous glucose monitoring. Embodiments of a glucose monitoring device comprise a sensor element positioned in a location where surface area and volume of the sensor element is maximized. Conventional percutaneous sensors cannot appreciably increase their surface area and volume without causing pain and discomfort and while risking sensor performance due to biological responses. Further, conventional implantable intravascular enzymatic sensors have limited sensing surface areas and thicknesses. Embodiments of the present specification overcome these limitations by making use of sensing surface areas that are orders of magnitude larger than that of conventional sensors while concurrently not requiring excessively thick enzyme layers, thereby not adding unnecessary diffusion delays. The increased surface area, coupled with a marginally increased enzyme layer, of the presently disclosed embodiments, enable glucose concentration measurement without significant noise levels while also increasing the amount of glucose oxidase. Furthermore, any decrease in glucose diffusion effectively increases relative enzyme concentration while also reducing the oxidation/reduction cycles, thereby potentially increasing glucose oxidase longevity and sensor life while measuring sufficient amount of current providing a decent signal to noise ratio.

The present specification describes an implanted intravascular sensor approach that minimizes occlusion and has sufficient blood flow to the sensing element, thus ensuring proper conditions for stable glucose measurement. In embodiments, a positioning element is deployed in or around the sensing element. The positioning element enables sufficient exposure of the sensing element to the blood flow while also preventing the sensing element from getting too close to the vessel wall. In one embodiment, a Nitinol structure is employed at either end of the sensing element, or over the entire sensing element itself, to position the sensing element sufficiently near the center of the vessel. Embodiments of the present specification limit any variations in blood glucose exposure due to patient posture, patient motion, and/or lead movement due to circulatory dynamics. The embodiments also minimize the chance for any clots by keeping the sensor within a venous vessel at a location of consistently high blood flow. Moreover, the Nitinol structure can be employed within a lead body of the sensor element itself, either proximal and/or distal to the working electrode, thereby integrally forming the lead body and the positioning element and minimizing exposure of the Nitinol element to the vasculature.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise", "include", "have", "contain", and forms thereof, are not necessarily limited to members in a list with which the words may be associated. Thus, they are intended to be equivalent in meaning and be open-ended in that an item or items following any one of these words is not meant to be an exhaustive listing of such item or items, or meant to be limited to only the listed item or items. It should be noted herein that any feature or component described in association with a specific embodiment may be used and implemented with any other embodiment unless clearly indicated otherwise.

The phrase "one or more of X, Y, and Z" in the claims shall be interpreted to mean X or Y or Z or any combination of X, Y and Z.

It must also be noted that as used herein and in the appended claims, the singular forms "a," "an," and "the" include plural references unless the context dictates otherwise. Although any systems and methods similar or equivalent to those described herein can be used in the practice or testing of embodiments of the present disclosure, the preferred, systems and methods are now described.

FIG. 1 illustrates an exemplary layout of a continuous glucose sensor 100 comprising a glucose sensor lead assembly 110 and a hermetically sealed glucose sensor electronics assembly 120, in accordance with some embodiments of the present specification. Glucose sensor lead assembly 110 is connected to the glucose sensor electronics assembly 120 using known implantable device connection methods. Examples of connectors used may include, and are not limited to, connector assemblies specified by the standard ISO 5841-3:2013, which are typically used for connecting a cardiac lead to a cardiac pacemaker, and connector assemblies used in spinal cord stimulators. Additionally, the glucose sensor electronics assembly 120 is shaped to minimize skin incision size and number of sutures. In some cases, sutures are not used and glue is used. In one embodiment, the glucose sensor electronics assembly 120 has a form factor in a range of 1 cc to 25 cc of volume and/or a dimensional range of 20 mm×5 mm×1 mm to 50 mm×10 mm×5 mm, more preferably around 45.1 mm×8.0 mm×4.2 mm.

The glucose sensor 100 uses electrochemical analysis methods to quantify the glucose levels through an implanted device. Sensor lead assembly 110 includes one or more enzyme-based electrochemical sensors. The sensors herein, also known as amperometric glucose sensors, contain one or more electrodes that measure the current generated by an enzymatic reaction between glucose, an enzyme, and a mediator. The enzyme layer is provided over the surface area of the electrode(s), and may include glucose oxidase. As a result of the electrochemical enzymatic reaction, the glucose is converted into a byproduct that can be measured as a current. In some embodiments, the enzymatic sensing modality is based on use of one of the following: $H_2O_2$; $O_2$ differential; wired; or engineered. In some embodiments, the glucose sensor 100 is a non-enzymatic sensor that uses fluorescence or optics for its measurements. In some embodiments, the sensor 100 uses photodetectors, such as, but not limited to, photodiodes and fluorimeters. Optics based sensors may use LED light sources that are hermetically encapsulated in glass. In some embodiments, sensor 100 near-hermetic encapsulation is in optically-transparent polymers. The enclosures can incorporate coatings and/or materials with optical filtering capabilities. In some embodiments, sensor 100 uses glucose binding molecules for sensing.

Further, sensor electronics assembly 120 is configured within a separate housing and is in electrical communication with lead assembly 110. In some embodiments, some or all of sensor electronics assembly 120 is integrated with the lead assembly 110. During implanting of sensor 100, sensor electronics assembly 120 is positioned at proximal end in a subcutaneous pocket. The housing encompassing the electronics of sensor electronics assembly 120, when integrated with lead assembly 110, is configured to overcome mechanical noise or any other noise sources, such as those observed during low currents. In this case, the housing may not require hermetic encapsulation but requires potting in a polymer such as silicone or epoxy.

Figure 2A:
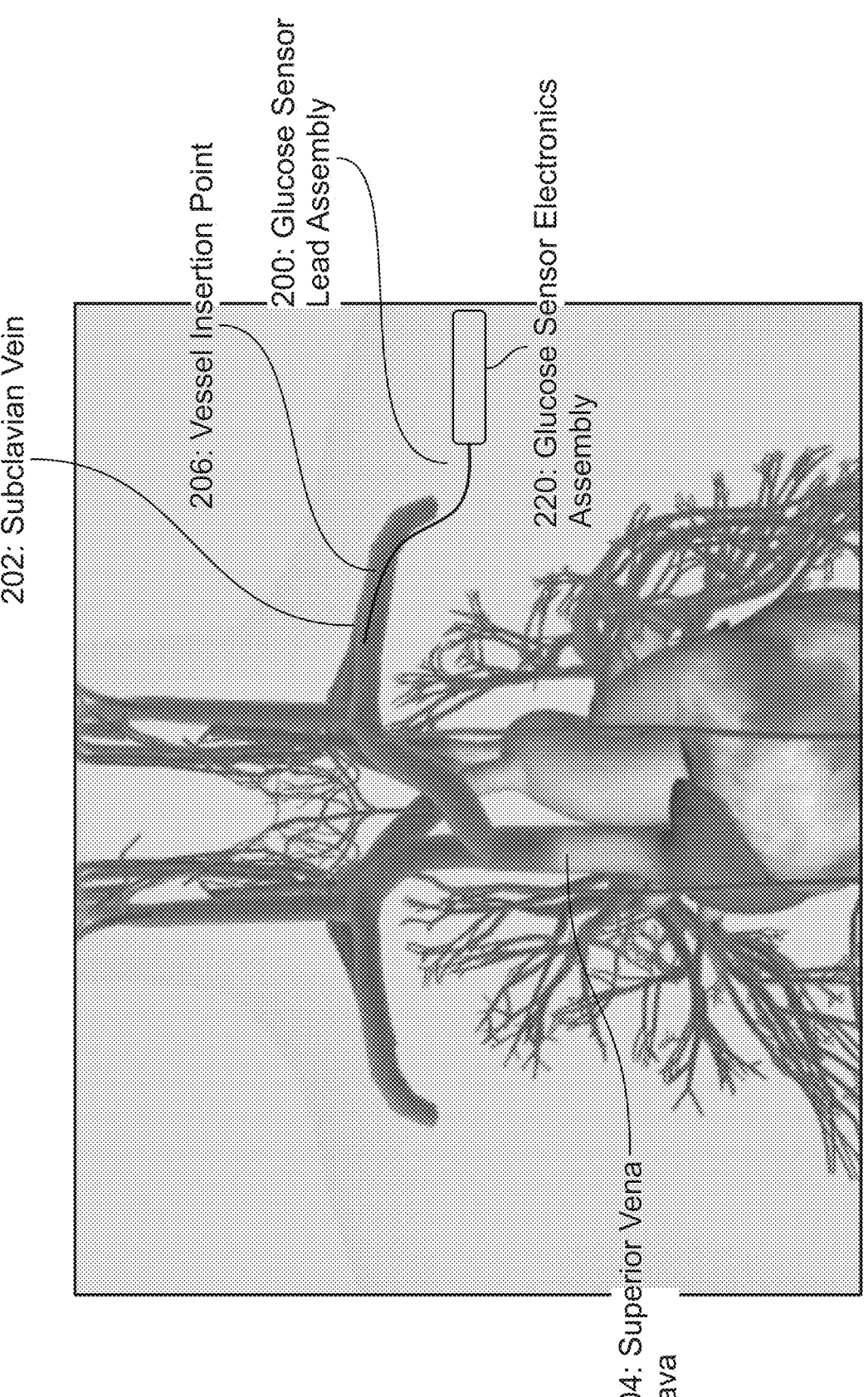
FIG. 2A illustrates a schematic of an exemplary placement of a glucose sensor lead assembly within a human anatomical structure, through a subclavian vein and extending prior to the subclavian/jugular vein juncture.

FIG. 2A illustrates a schematic of an exemplary placement of a glucose sensor lead assembly 200 (glucose sensor lead assembly 110 of FIG. 1) within a human anatomical structure, through a subclavian vein 202 all the way to the distal end of the superior vena cava 204. The glucose sensor lead assembly 200 is preferably designed so that it can be inserted at a vessel insertion point 206 through the subclavian vein 202 and subsequently resides in the subclavian vein 202. In some preferable cases, lead assembly 200 would enter the subclavian vein 202 where it passes over first rib near the rib's lateral border, so as to avoid the subclavian muscle and nearby ligament structures, or any other undue anatomical forces on the lead body that could lead to a fracture within the human anatomy. In some cases, lead assembly 200 is placed in the central venous system so that any potential clots resulting from the positioning and placement of assembly 200 travel to the lungs instead of the heart or brain. In embodiments, lead assembly 200 is placed in high blood-flow portions of the venous vasculature (not the peripheral vasculature) to prevent blood clotting. In embodiments, length of glucose sensor lead assembly 200 is configured such that a distal end of lead assembly 200 does not go past the superior vena cava 204. Preferably, the glucose sensor lead assembly 200 is designed such that the distal end of the lead assembly 200 does not go past the junction with the internal jugular vein of the human anatomy.

Figure 2B:
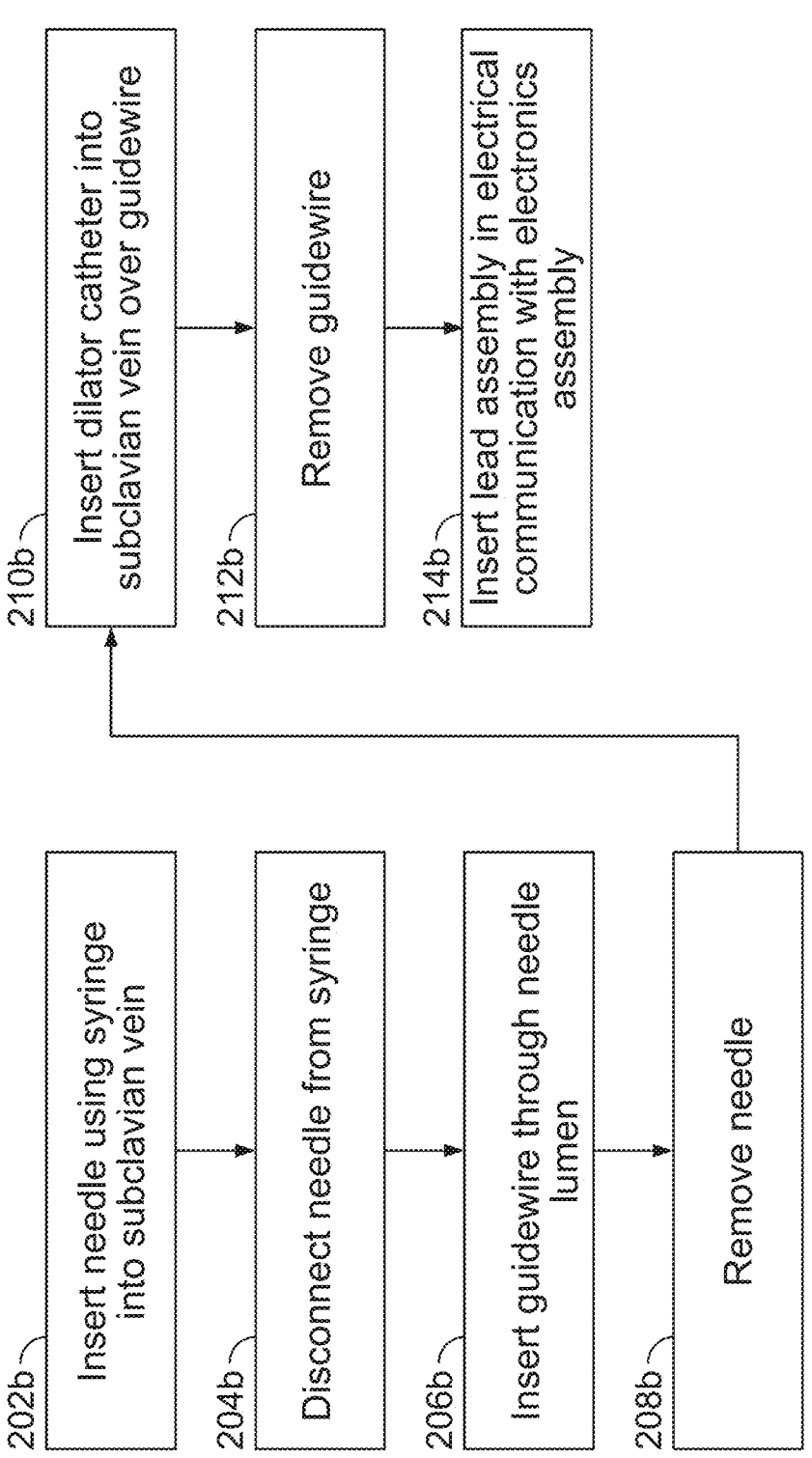
FIG. 2B illustrates an exemplary process of inserting a glucose sensor lead assembly inside a patient, in accordance with some embodiments of the present specification.

FIG. 2B illustrates an exemplary process of inserting and/or implanting the glucose sensor lead assembly 200 in accordance with some embodiments of the present specification. The glucose sensor lead assembly 200 insertion technique can be accomplished via a multi-step process that may or may not be guided by other medical diagnostic tools (e.g., ultrasound). The insertion technique begins at step 202b with a syringed needle puncture into the subclavian vein 202 by holding the syringe needle parallel to the body and clavicle while inserting it under the clavicle. The needle insertion position is approximately at the level of the top of the manubrium and about two-thirds distal of that just beyond the clavicle. Once blood has entered the syringe, the needle is properly placed in the subclavian vein 202. At step 204b, the syringe is then disconnected from the needle while holding the needle in its position. At step 206b, a guide wire is inserted through the lumen of the needle and then the needle is extracted at step 208b. An incision of approximately 1 to 2 centimeter (cm) is made to facilitate the entry of a dilator catheter and eventually the glucose sensor electronics assembly 200. At step 210b, the dilator catheter is inserted over the guide wire and into the subclavian vein 202, after which at step 212b, the guide wire is also removed. At step 214b, the glucose sensor lead assembly 200 is inserted through the dilator catheter until it is in the subclavian vein 202 at a sufficient depth. The depth of insertion of lead assembly 200 can be determined with visual indicators, such as markings (for example, cm markings), on the guidewire, the dilator catheter, and glucose sensor lead assembly 200. Once inserted, a portion of proximal end of the glucose sensor lead assembly 200 is positioned to temporarily remain outside the human body. A tunneling tube is used to create a subcutaneous pocket for a glucose sensor electronics assembly 220 so that the pocket is created beginning at the incision made earlier at a depth of 1 to 2 cm. The glucose sensor lead assembly 200 is connected to the glucose sensor electronics assembly 220 at the proximal end of the lead assembly 200. The glucose sensor electronics assembly 220 is inserted into the subcutaneous pocket, thus making the entire glucose sensor assembly, including lead assembly 200 and electronics assembly 220, implanted within the human anatomy. The incision is subsequently closed using sutures, suture tape, or suture glue.

In some cases, the continuous glucose sensor of the present specification is positioned within the central venous vasculature through the subclavian vein and superior vena cava as illustrated in FIG. 2. In some other cases, the continuous glucose sensor of the present specification is positioned within the peripheral venous vasculature, such as through arms or legs. In the case of peripheral venous vasculature, sufficient mechanisms are included in the configuration of the glucose sensor device to prevent clotting. In an embodiment, a heparin coating is used with the sensor device to prevent clotting. In other embodiments, the continuous glucose sensor of the present specification is positioned within the spinal column to measure glucose levels in the cerebrospinal fluid.

Figure 3:
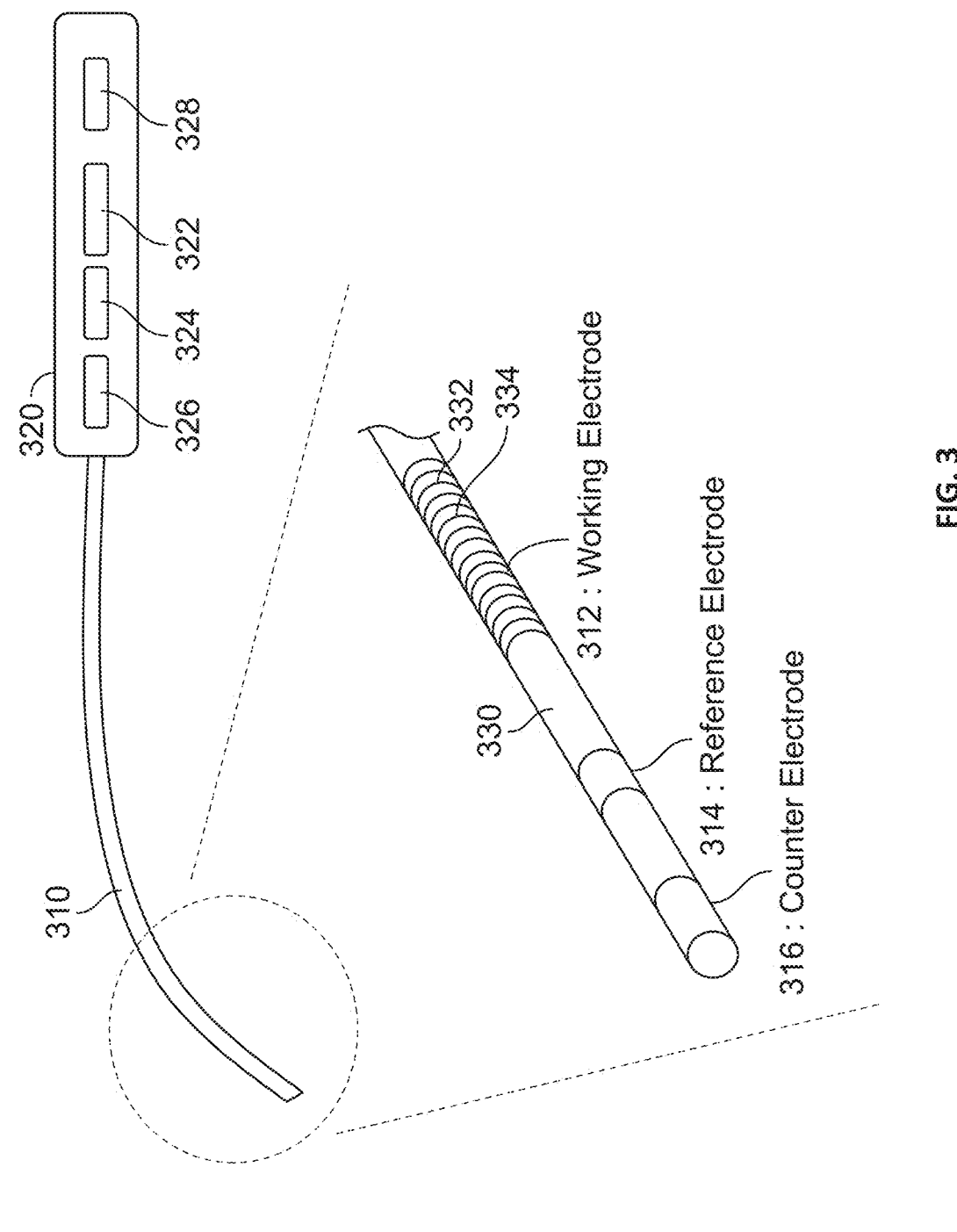
FIG. 3 illustrates a continuous glucose sensor comprising a sensor lead assembly connected to a sensor electronics assembly in accordance with some embodiments of the present specification.

FIG. 3 illustrates a continuous glucose sensor 300 comprising a sensor lead assembly 310 connected to a sensor electronics assembly 320, in accordance with some embodiments of the present specification. The figure further illustrates a blown-out schematic representation of a distal portion of the sensor lead assembly 310. The sensor lead assembly includes an elongated central shaft 330. In some embodiments, at least three electrodes are configured in physical communication with the surface of central shaft 330 sequentially along the length of shaft 330. Sensor lead assembly 310 comprises three electrodes: a working electrode 312, a reference electrode 314, and a counter electrode 316. In an embodiment, a distal coil (working electrode 312, 712) with a surface are of 150 mm² is employed along with reference electrode (314, 714) and a proximal coil (counter electrode 316, 716) with a surface area that is at least 1.5 times greater than the surface area of the distal coil. In another embodiment, a distal coil (working electrode 312, 712) with a surface area of 150 mm² is employed along with a combined reference and counter electrode with a surface area that is at least 1.5 times smaller than that of working electrode 312/712.

The working electrode 312 is the electrode that is where the reaction with glucose takes place, where the reaction is of interest to control or to investigate. In some embodiments, working electrode 312 measures hydrogen peroxide (H₂O₂) to monitor glucose levels. In some embodiments, working electrode 312 is made using platinum. In some embodiments, working electrode 312 is positioned at the distal end of lead assembly 310 and is configured to cover the distal end of assembly 310 in the form of a boot or an endcap. In some embodiments, working electrode 312 comprises one electrode, or two or more electrodes, where each working electrode 312 is covered with separate bioresorbable membranes. The membranes can include mechanical adhesion-promoting features, such as for example those that enable covalent bonding with substrate. The electrodes may include multiple working electrodes 312 to sense for glucose and/or other analytes, such as pO2 or pH, and/or is used to assess oxygen fluctuation impact on glucose measurements.

Reference electrode 314 is configured to deliver a constant potential with no current flowing through it to enable its monitor and control. In some embodiments, reference electrode 314 is made using silver-silver chloride (Ag/AgCl).

Counter electrode 316 is an inert metal or carbon species with a larger surface than working electrode 312 to complete the ionic/electronic current pathway. In some embodiments, counter electrode 316 is made using Platinum. In some embodiments, counter electrode 316 is positioned at the distal end of lead assembly 310 and is configured to cover the distal end of assembly 310 in the form of a boot or an endcap. In some embodiments, counter electrode 316 includes a hermetic metallic housing of electronics to simplify the connection scheme, lead design, and reduce costs.

While the figure illustrates the counter electrode 316 positioned at the distal end of sensor lead assembly 310 and the working electrode 312 at a proximal side of the sensor lead assembly 310, the two electrode positions are interchangeable in different embodiments. Further, in embodiments, one or more of electrodes 312, 314, and 316 may take the shape of a coil or a bulk metal structure. In some embodiments, an electrode is not configured at the distal end of sensor lead assembly 310. In some other embodiments the number of electrodes is less than or more than three. In one embodiment, there is only a working electrode 312 and a reference electrode 314, the latter of which also functions as a counter electrode by allowing current to pass through it. In one embodiment, the sensor lead assembly 310 comprises a large coil working electrode 312 and two ring electrodes shown as the reference electrode 314 and the counter electrode 316. In some embodiments, sensor lead assembly 310 also includes a standard connection system, such as and not limited to a DF-4 connector, to enable connection to sensor electronics assembly 320.

In embodiments, counter electrode 316 and reference electrode 314 are made of platinum or a similar noble metal. Some embodiments of reference electrode 314 include a silver-silver chloride coating, or iridium oxide. Working electrode 312 includes a coil made of platinum or a similar noble metal or a noble metal alloy. In some embodiments, working electrode 312 includes an outer membrane that controls the diffusion of glucose. In some embodiments, working electrode 312 includes an inner membrane coating that incorporates immobilized glucose oxidase. In a two-membrane system of the present specification, the outermost (tissue-facing) membrane 332 is the glucose limiting membrane. The innermost (electrode-facing) membrane 334 is the immobilized glucose oxidase membrane. Some embodiments include other membranes, for example interferent membranes, for acetaminophen and ascorbic acid. The other membranes can be located anywhere in the chain of membranes, depending on their role or function. In some embodiments, the additional membranes enable anti-clotting functions, such as, for example, microarchitecture or dexamethasone. Some embodiments include additional membranes that are analyte-specific, for example, ketones and lactate. In embodiments, working electrode 312 is covered entirely by the membrane(s). In some cases, the membrane coating(s) extend beyond the working electrode 312 as well but does not cover the reference electrode 314.

In various embodiments, any one or more of the electrodes 312, 314, and 316, is configured similar to a ring electrode of a cardiac pacemaker lead, a ring electrode of a spinal cord stimulator lead, or a paddle electrode of a spinal cord stimulator lead. In some embodiments, one or more of electrodes 312, 314, 316, are constructed from conductive polymers or carbon nanotubes. In some embodiments, any one or more of the electrodes 312, 314, 316 comprises multiple physical electrodes that are electrically connected. For example, in an embodiment, two separate rings are used to make one working electrode wherein the two separate rings are electrically connected. In some embodiments, surface(s) of one or more of electrodes 312, 314, and 316, are roughened or pitted to increase their surface area.

Further, shaft 330 of lead assembly includes at least one positioning element made preferably using a shape-memory element, such as, for example Nitinol. Each positioning element is linearly placed inside lumen or shaft 330 in an undeployed state, and changes its shape to extend away from shaft 330 when deployed by enabling a distal end of the positioning element to move outwards from the shaft 330. FIGS. 6 to 11 illustrate deployed configurations of one or more positioning elements in accordance with embodiments of the present specification.

Electronics assembly 320 can be similar to that of any conventional implanted pacemaker or neurostimulator, using similar material and construction processes and housing electronics and a battery, while also including a connector configuration that corresponds to the connection mechanism of lead assembly 310. Embodiments of electronics assembly 320 include a potentiostat that interfaces with the three electrodes 312, 314, and 316. The potentiostat provides sufficient voltage bias between the working electrode 312 and the reference electrode 314 to measure hydrogen peroxide, which is the byproduct of the glucose oxidase catalyzation of glucose and oxygen. The potentiostat also measures current generated by the electrodes, resulting from a measurement of hydrogen peroxide, and converts it to a voltage that can be filtered to remove noise. The filtered voltage signal is further digitized by an analog to digital converter. The resulting digital data is filtered and prepared for transmission to a smartphone, tablet, or other such computing device using a wired or a wireless connection, such as for example a Bluetooth wireless communication protocol. Some embodiments of electronics assembly 320 include an accelerometer 322 which is used to generate data indicative of a physical orientation of the wearer or carrier of the glucose monitoring device 300. Data from the accelerometer 322 is used to trigger a measurement. In one exemplary scenario, the sensor is triggered to measure glucose during a period of time when the wearer is relatively still. In some embodiments, electronics assembly 320 includes a sensory alarm 324 such as a mechanism to vibrate, when the patient reaches a specified high or low glucose limit. All of these processes are controlled by a programmed microcontroller 326 running firmware and included in the electronics assembly 320.

Figure 4:
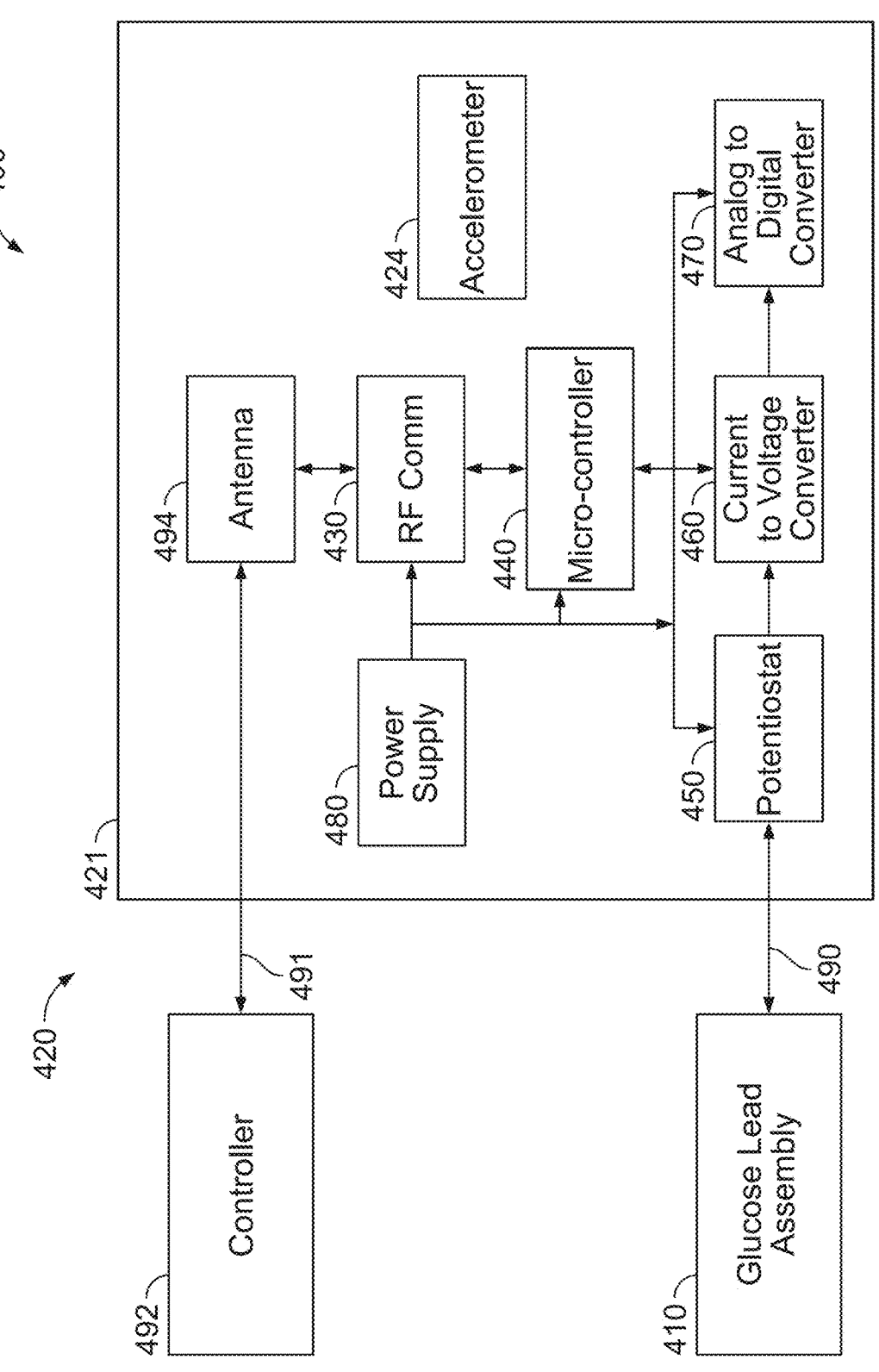
FIG. 4 illustrates an exemplary schematic of components in an electronics assembly and its connections, in accordance with some embodiments of the present specification.

FIG. 4 illustrates an exemplary schematic 400 of components in an electronics assembly 420 (electronics assembly 320 of FIG. 3) and its connections, in accordance with some embodiments of the present specification. The electronics and power components are contained within a housing 421 of the electronics assembly 420. The housing 421 interfaces with a glucose sensor lead assembly 410 through a connection 490. In some embodiments, the connection 490 between sensor lead assembly 410 and electronics assembly 420 is enabled using three conductors, one each for the electrodes 312, 314, 316 described with reference to FIG. 3. In some embodiments, electronics assembly 420 interfaces with an external controller 492 via a wired or wireless communication link 491. In some embodiments, link 491 is a bidirectional Bluetooth signal for communicating with a Bluetooth-enabled smartphone or tablet (controller 492), or any other external handheld device. In some embodiments, the communication link 491 is enabled over a WiFi connection with direct communication to a smartphone and/or tablet or to an external handheld device.

Electronics assembly 420 houses a power supply 480. In some embodiments power supply 480 comprises a housing for one or more batteries that may be rechargeable and/or replaceable. In some embodiments, the battery is a primary, non-rechargeable cell such as LiCFx. In some embodiments, the battery is a rechargeable cell such as Li-ion. Embodiments of the rechargeable battery can be charged using inductive coupling methods, radio-frequency (RF), or far-field techniques. Some embodiments include a power supply regulator, such as a voltage regulator, along with a safety mechanism such as a fuse with the power supply 480. The voltage regulator maintains a stable power delivery while the fuse prevents any internal short circuit and subsequent device heating. Power supply 480 powers all the electronic components of electronics assembly 420. The other components within electronics assembly 420 include a microcontroller 440, a potentiostat 450, a current to voltage converter 460, an analog to digital converter 470, and an RF communication circuit 430. Potentiostat 450 provides sufficient voltage bias between the working electrode 312 and the reference electrode 314 to measure hydrogen peroxide, which is the byproduct of the glucose oxidase catalyzation of glucose and oxygen. Potentiostat 450 also measures current generated by the electrodes of the lead assembly 410, resulting from a measurement of hydrogen peroxide. Current to voltage convertor 460 converts the current to a voltage signal that is filtered to remove noise. The filtered voltage signal is further digitized by analog to digital converter 470. The resulting digital data is filtered and prepared for transmission using RF communication circuit 430 to a controller 492. The RF communication circuit 430 is in data communication with an antenna 494 to communicate with controller 492. In some embodiments, that current to voltage converter 460 and analog to digital converter 470 are integrated within microcontroller 440. Moreover, all electronic components illustrated and described herein could be integrated into a single chip system. Microcontroller 440 interfaces with the other electronic components within electronics assembly 420 to specify their operational parameters, obtain diagnostic information from them, and receive any other type of necessary data. In some embodiments, an accelerometer 424 is included in the components of electronics assembly 420.

In alternative embodiments, a combination of the following is integrated in lead assembly 410: potentiostat; potentiostat and ADC, potentiostat, ADC, and components for digital communication; potentiostat, ADC, components for digital communication, and microcontroller; and optical sensing systems such as and not limited to photodiodes. In an alternative embodiment, potentiostat 450 and current to voltage converter 460 are configured in sensor lead assembly 410. In this embodiment, connection 490 is configured to provide power supply and ground from electronics assembly 420 to potentiostat 450 and current to voltage converter 460 while receiving a voltage representative of measured current at the working electrode 312 from lead assembly 410. In some embodiments, analog to digital converter 470 is also configured in the sensor lead assembly 410 under which condition the voltage signal is removed from connection 490 and replaced by a digital interface communication circuit such as a conventional I2C or SPI or any other conventional or custom interface. In these alternative embodiments, electronic components configured in the sensor lead assembly 410 are encapsulated within a protective housing to protect them from biological fluids and blood flow.

In some embodiments, optical measurement technologies are used in the monitoring device. Optical measurement technologies may include infrared or fluorescence sensors using glucose-activated fluorescing compounds such as boronic acid. Embodiments of the optical sensors have a similar structure and components to those described with reference to FIGS. 1, 3 and 4, except that sensor lead assembly 310 (of FIG. 3) employs optical sensors in a hermetically-sealed glass or near-hermetically sealed polymer housings, in place of electrodes. In embodiments, the housings are optically transparent at wavelengths ranging from 300 nanometers (nm) to 800 nm. Moreover, the housings may incorporate coating and/or materials with desired optical filtering properties so as to allow a specific range of optical wavelengths to pass through the housings while restricting other wavelengths. One embodiment employs one optical sensor to measure the optical signal correlated to glucose concentration. Another embodiment employs two or more optical sensors to enhance the signal to noise ratio. In embodiments using two or more optical sensors, the sensors are configured with similar optical sensing properties (for example, the wavelength sensing properties) to facilitate algorithmic assessment of glucose concentration via statistical methods. In some other embodiments, the two or more sensors have different optical sensing properties to facilitate algorithmic assessment of glucose concentration via detection of background and/or interfering species in the blood. In yet other embodiments, multiple optical sensors are used where some sensors have similar and some other have different optical sensing properties, so as to accomplish both the tasks described above. Another embodiment additionally incorporates a light emitting source to provide a baseline for measurement within the blood. Another embodiment additionally incorporates a light emitting source to act as an excitation source for the fluorescing agent. The optical sensing and emitting elements employed in the above embodiments are any of the following: infrared sensors, LEDs and photodiodes, and fluorimeters. Optical sensor measurements are processed by circuitry that can interface with the optical components described herein, replacing potentiostat 450 and current to voltage converter 460 of FIG. 4 in some of the embodiments.

Embodiments of the glucose sensor are calibrated in order to accurately be able to determine a glucose concentration from a measured current. The current, therefore, is converted to a glucose concentration via a calibration factor or set of calibration factors. The glucose sensor is preferably factory-calibrated at the time of manufacturing, so that the user does not need to provide any venous blood samples for glucose measurement for the purpose of calibrating the measured glucose sensor current to the actual blood glucose concentration. In some embodiments the monitoring device is configured for one-time user calibration that would occur post-implantation of the monitoring device. In the embodiment for one-time user calibration, the user (wearer/carrier) can provide calibrating blood glucose data from a standard single point measurement, such as for example using a traditional finger stick device and method, or from other percutaneous continuous glucose sensors. Either technique requires the user to record the data into a supporting application executed on a computing device such as a smartphone, which will process the recorded data and communicate the processed calibration factors to the implanted electronics assembly of the monitoring device. In some cases, a physician performs the one-time calibration in a clinic environment using an intravenous measurement technique. The physician may also manipulate the user's blood glucose levels by requiring a standard oral glucose tolerance test or a similar method. In some embodiments, an algorithm is employed to predict any glucose sensor output degradation or variability over time and adjust the estimated glucose values accordingly.

FIGS. 5 to 10 illustrate different embodiments of a sensor lead assembly 310 (of FIG. 3). Specifically, the embodiments describe configurations of a positioning element that may comprise shape-memory alloy (for example, Nitinol) structures. The embodiments illustrate and describe the different Nitinol configurations for an implanted lead assembly 310 that is positioned inside a human anatomy. Nitinol structures are configured on either side of or surround one or more of electrodes of the lead assembly 310. In one embodiment, the Nitinol structure is substantially linear and positioned inside a catheter. In another embodiment, the Nitinol structure extends laterally out from the lead assembly 310 and is configured to touch, but not put undue pressure on, the vessel wall. The Nitinol structure is configured to keep the working electrode (electrode 312 of FIG. 3) centered in the vessel to enable proper flow of blood around it and prevent any possible adherence of lead assembly 310 to the vessel wall due to user's movement, change in posture, or blood circulatory dynamics within the vessel.

Figure 5:
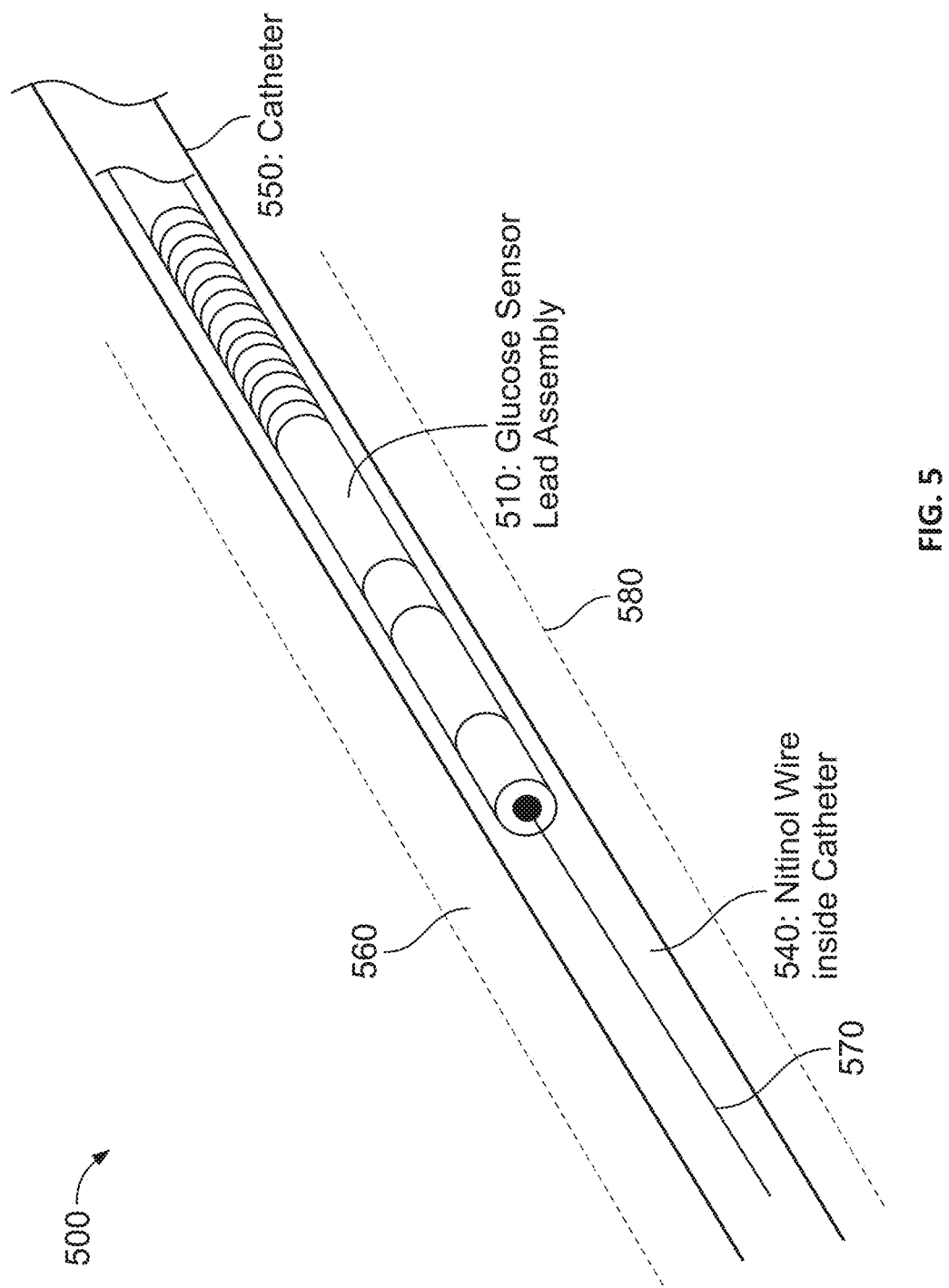
FIG. 5 illustrates a schematic of an embodiment of a positioning element positioned within a glucose sensor lead assembly, within a delivery catheter prior to deployment, in accordance with some embodiments of the present specification.

FIG. 5 illustrates a schematic of an embodiment of a positioning element 540 positioned within a glucose sensor lead assembly 510, in accordance with some embodiments of the present specification. Lead assembly 510 containing positioning element 540 is deployed through a lumen of a catheter 550 that is positioned in a blood vessel 560. Positioning element 540 is preferably made from Nitinol and is structured linearly like a straight wire when undeployed. During deployment of positioning element 540, it is extended outwards from the distal end of lead assembly 510. When deployed, distal portion of positioning element 540 may reform into a spiral, a hook, or a loop.

Figure 6:
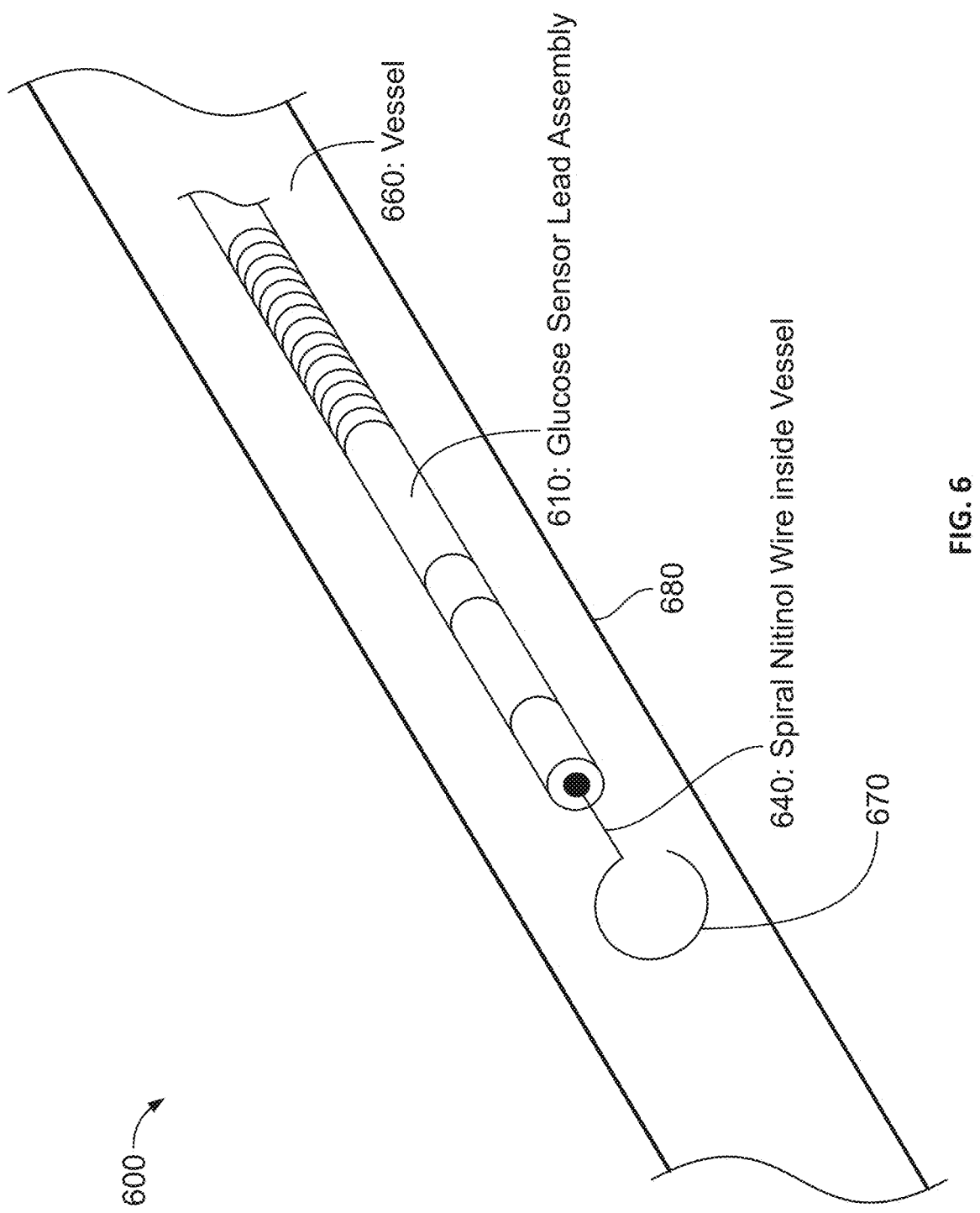
FIG. 6 illustrates an embodiment of a deployed positioning element deployed through lead assembly and placed within a vessel.

In one embodiment, in its smallest, uncompressed state, the spiral, the hook, or the loop diameter is at least 10% less than diameter of wall of vessel 560. Distal end 570 of the spiral, hook, or loop, once deployed, is configured to ensure that no trauma is caused to wall of vessel 560. FIG. 6 illustrates an embodiment of a curved end 670 of a positioning element 640 deployed through lead assembly 610 and placed within a vessel 660. In embodiments, the distal tip is configured with an end cap, is polished, includes an atraumatic tip, and/or may include a bend toward the lumen of vessel 660. The tip is configured to ensure that the internal wall 680 of vessel 660 is not affected, for example, by a scratch or any form of a puncture. The spiral, hook, or loop can be in a single plane (as shown in FIG. 6) or stretched out (in the form of a coil). The spiral, hook, or loop can loop back, at least partially, to its origin to form a circular or elliptical spiral. It should be appreciated that the purpose of the positioning element 640 is to position the electrodes of lead assembly 610 within 7 mm of the center of the vessel 660 and to rarely, and preferably never, contact the vessel wall 680. It should further be appreciated that the positioning element 640 exerts no more than 0.01N on the vessel wall 680 to avoid damaging the vessel wall 680 to position the electrodes within 7 mm of the center of the vessel 660.

Embodiments of the present specification thus ensure that while positioning the electrode(s) of lead assembly 610 away from the vessel wall 680, no undue pressure is applied on the vessel wall 680. This is necessary to prevent any stenosis of the vessel wall 680 by significant contact of the positioning element 640 with the vessel wall 680 (typical vascular stents are known to cause stenosis over time). To reduce contact with the vessel wall (and reduce chance of stenosis), the diameter of the positioning element 640 is at least 10% smaller than the smallest diameter of the vessel 660 lumen. The measure of smallest diameter is relative to the smallest state of the vessel 660 under any physiological condition such as due to heart rate, neurohormonal responses, temperature, or any other condition.

Further contact with the vessel wall 680 is reduced by avoiding the conventional woven structure for the positioning element 640. Embodiments of positioning element 640 of the present specification uses as little shape-memory wire (such as Nitinol) as possible. More specifically, it is desired to not have more than one positioning element 640 in contact with the vessel wall 680. Further the contact with vessel wall 680 is in such a manner so that at any time length of Nitinol wire element positioned in the lumen of vessel 660 is no more than 12 cm, preferably less than 6 cm, and more preferably less than 3 cm. Moreover, the diameter that is at least 10% less than the diameter of the vessel 660 lumen ensures that no more than 35% of the overall Nitinol wire element is in contact with the vessel wall 680 at any point in time. Size and position configurations of positioning element 640 in accordance with embodiments of the present specification has the added benefit of minimizing any possible disruption to blood flow within the vessel 660. More specifically, the positioning element 640 is in the blood flow since it is not pressed against the vessel wall 680. Additionally, the positioning element 640 provides less material for any possible clotting to occur. In some embodiments, positioning element may be coated with some pharmacological material to prevent stenosis, such as dexamethasone or some non-pharmacological hydrophobic material. Contact of positioning element 640 with wall 680 of vessel 660 is further minimized by positioning the positioning element 640 within body of lead assembly 610, either proximal and/or distal to the working electrode.

Figure 7:
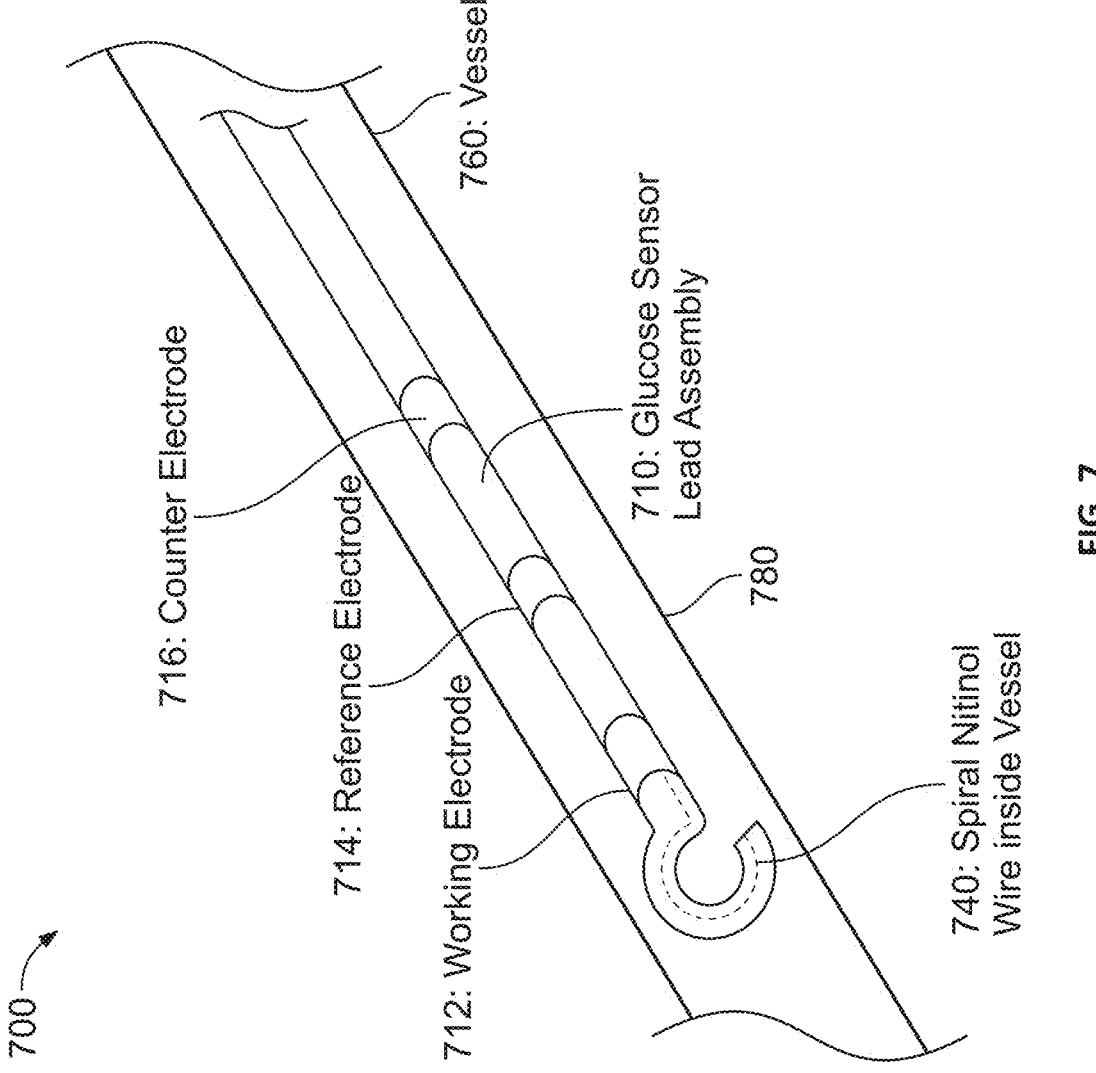
FIG. 7 illustrates an embodiment of a positioning element that is embedded within a lumen of lead assembly distal to working electrode, in accordance with some embodiments of the present specification.

FIG. 7 illustrates an embodiment of a positioning element 740 that is embedded within a lumen of lead assembly 710 distal to working electrode 712, in accordance with the present specification. Accordingly, specific non-electrode portions of the lumen or body of lead assembly 710 are configured to take a coil/spiral shape to create the centering effect as described above while not exposing the positioning element 740 to the vessel wall 780. Moreover, a coiled lead structure similar to that shown in FIG. 7 also acts as a stopping mechanism to prevent the lead assembly 710 from retreating out of vessel 760. Further, the shape-memory element forming positioning element 740 is within center of the lumen of lead assembly 710, while the electrodes 712, 714, and 716 are constructed like those of typical cardiac leads using coaxial MP35N coils with silicone insulation between them. The electrodes configuration provides significant mechanical protection to ensure that the shape-memory element does not protrude out from the body of lead assembly 710. Alternatively, the shape-memory element structure is positioned at the distal portion of lead assembly 710, distal to the electrodes 712, 714, and 716, where different protection mechanisms may or may not be used.

Referring again to FIG. 6, in embodiments, distal end 670 of positioning element 640 does not place any uniform pressure on the internal lumen circumference of vessel 660 (like stents typically do to keep a lumen open). The pressure placed by distal end 670 of the positioning element 640 against the wall 680 of vessel 660 wall is at one or two contact points that are created by gravity and due to patient (user/wearer) position. The maximum force against the vessel wall at the contact point will be that due to gravity pulling on a portion of the glucose sensor lead assembly. More specifically, the portion of the lead assembly 610 that could exert force to due to gravity onto the vessel wall 680 would be that of the distal end 670 of the positioning element 640 in combination with a portion of proximal lead assembly 610, having a length ranging from 1 to 20 centimeters (cm), and/or having a mass of up to 1 gram. As such, the maximum force can be calculated to be 0.01N. Moreover, the contact point(s) may change (due to patient position) throughout an entire day, thereby further limiting any chance for stenosis at a single contact point. Other embodiments of the positioning elements 640 are shown in FIGS. 8 to 11.

Figure 8:
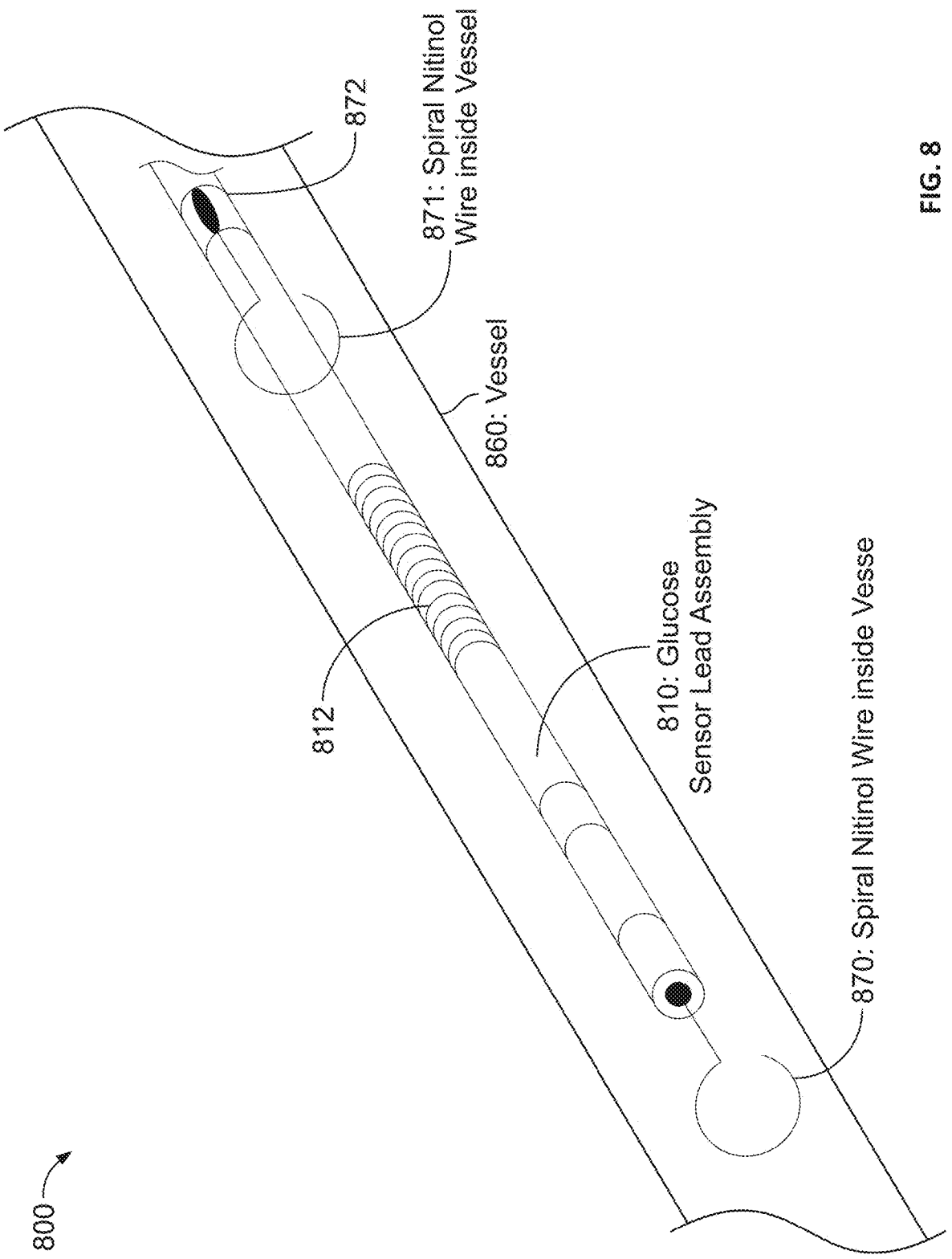
FIG. 8 illustrates a glucose sensor lead assembly comprising two spiral shape-memory elements and positioned inside a lumen of a blood vessel, in accordance with some embodiments of the present specification.

FIG. 8 illustrates an embodiment 800 of a glucose sensor lead assembly 810 positioned inside lumen of a blood vessel 860 and comprising two spiral shape-memory elements 870, 871, in accordance with some embodiments of the present specification. First shape-memory element 870 is positioned on a distal side of a working electrode 812 and extends from a center of lead assembly 810 at the distal end of lead assembly 810. Second shape-memory element 871 is positioned on a proximal side of working electrode 812. In embodiments, second shape-memory element 871 is attached to a ring 872 configured around the cylindrical outer surface of lead assembly 810. In some embodiments, diameter of ring 872 is the same as that of outer surface of lead assembly 810. Ring 872 can be made from the same materials as reference electrode 314 and/or counter electrode 316 (see FIG. 3). In embodiments, a length of ring 872 ranges from 0.5 mm to 10 mm. Element 871 is spot welded for attachment to ring 872 in an embodiment. The wire of element 871 extends alongside body of lead assembly 810 in a linear fashion, being held that way by the catheter that was used pre-deployment. Both shape-memory elements are made from Nitinol and form positioning elements to ensure that the working electrode 812 rarely touches internal wall of vessel 860. The two elements 870, 871 can be moved along a linear axis of the lead assembly 810.

Figure 9:
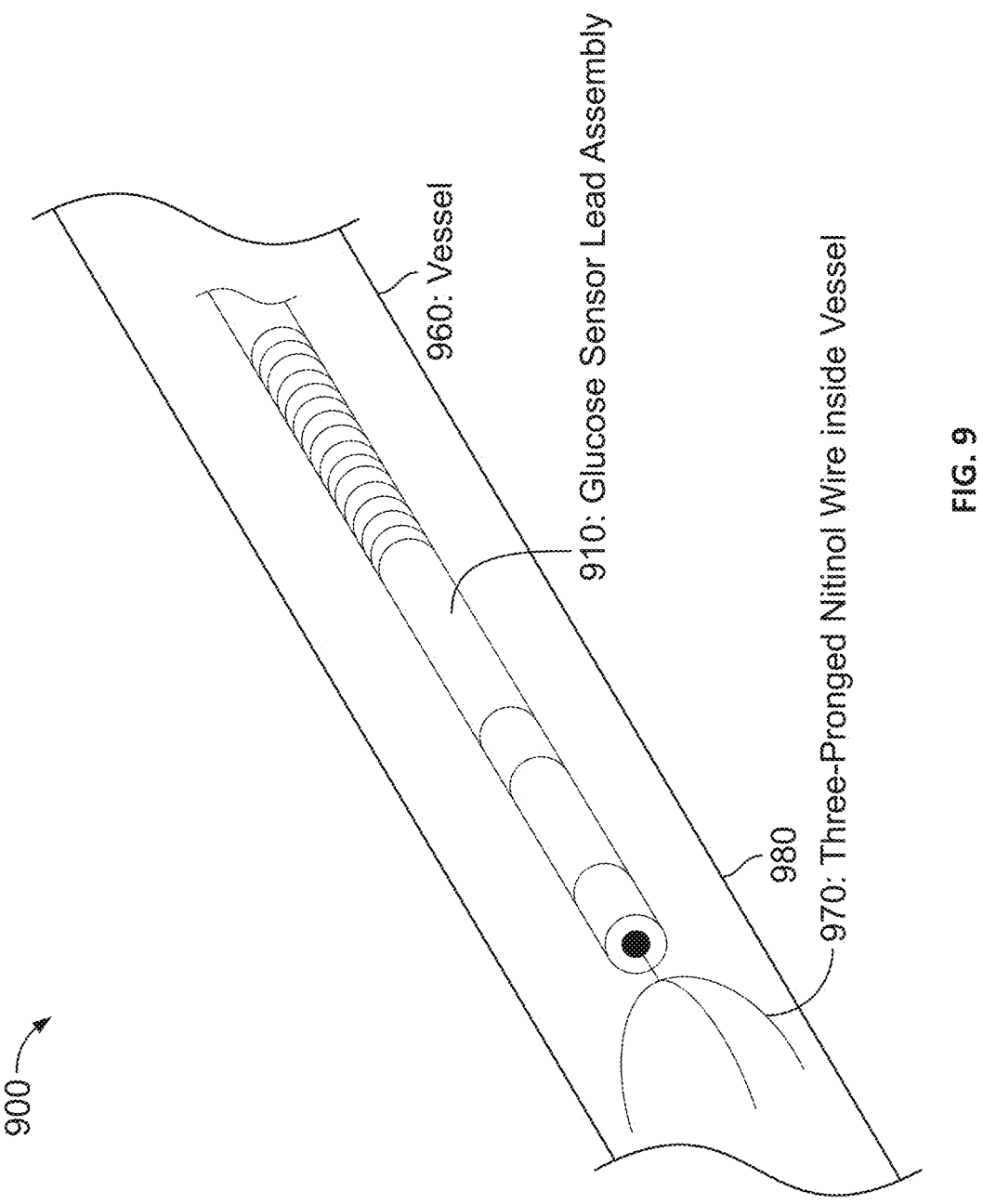
FIG. 9 illustrates an embodiment of a glucose sensor lead assembly comprising a three-pronged shape-memory element and positioned inside a lumen of a blood vessel, in accordance with some embodiments of the present specification.

FIG. 9 illustrates an embodiment 900 of a glucose sensor lead assembly 910 positioned inside lumen of a blood vessel 960 and comprising a three-pronged shape-memory element 970, in accordance with some embodiments of the present specification. Each prong of the pronged shape-memory element 970 extends for a length that ranges from 0.5 mm to 10 mm. The three-pronged shape-memory element 970 is made from Nitinol and is positioned at the distal end of the lead assembly 910. Each prong of element 970 may be configured with an atraumatic end to prevent puncturing of vessel wall 980. In some embodiments, each prong is formed in a loop. In embodiments, the loop formed by each prong is narrow (almond-shaped) or long (petal-shaped). In some embodiments, the prongs are configured to be linear towards their distal portions and curved in the portion tending towards the arc apex. The prongs stop curving before or at arc apex. In some embodiments, each prong has a curvature that continues past the arc apex and continues to bend back into towards the vessel 960. In embodiments, a maximum diameter of the prong assembly formed by element 970 is at least 10% less than diameter of internal wall of vessel 960 in its smallest state. The three prongs of element 970 are equally spaced at 120° from each other. In some embodiments, the number of prongs differ. In an embodiments, two prongs that are 180° apart are configured in the form of two half-spirals or in the shape of petals (looped). In another embodiment, four prongs are provided with each spaced 90° apart.

Therefore, embodiments of the present specification may include two or more prongs with their distal end extending away from a central shaft of sensor lead assembly 910. Furthermore, each prong is equally spaced radially around the central shaft. Additionally, each prong extends away from the remaining of the at least two or more prongs and from the central shaft.

Figure 10:
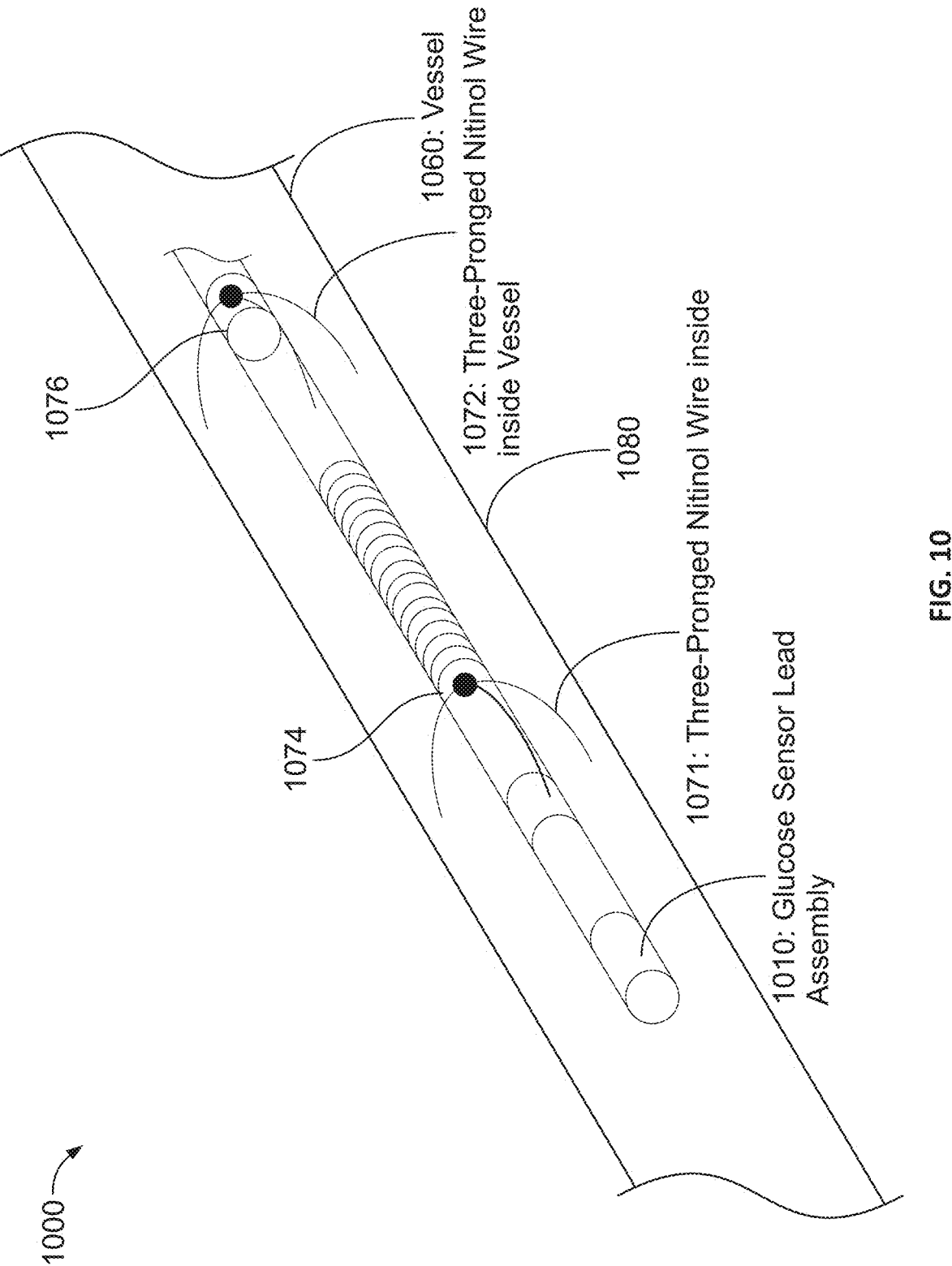
FIG. 10 illustrates an embodiment of a glucose sensor lead assembly comprising two three-pronged shape-memory elements and positioned inside a lumen of a blood vessel, in accordance with some embodiments of the present specification.

FIG. 10 illustrates an embodiment 1000 of a glucose sensor lead assembly 1010 positioned inside lumen of a blood vessel 1060 and comprising two three-pronged shape-memory elements 1071 and 1072, in accordance with some embodiments of the present specification. The two shape memory elements, in alternative embodiments, may have different number of prongs. In some embodiments, the two shape-memory elements may include a combination of a pronged element and a spiral element. Positions of the two elements 1071 and 1072 are changeable. The presence of two elements 1071 and 1072 ensure that the working electrode positioned within lead assembly 1010 does not touch the internal wall 1080 of vessel 1060. Rings 1074 and 1076, configured similar to ring 872 of FIG. 8, are provided on the surface of lead assembly 1010, to which the two elements 1071 and 1072 are respectively attached. The attachment is performed by way of spot welding, in an embodiment. In embodiments, a length of each prong is equal and ranges from 0.5 mm to 10 mm.

Figure 11:
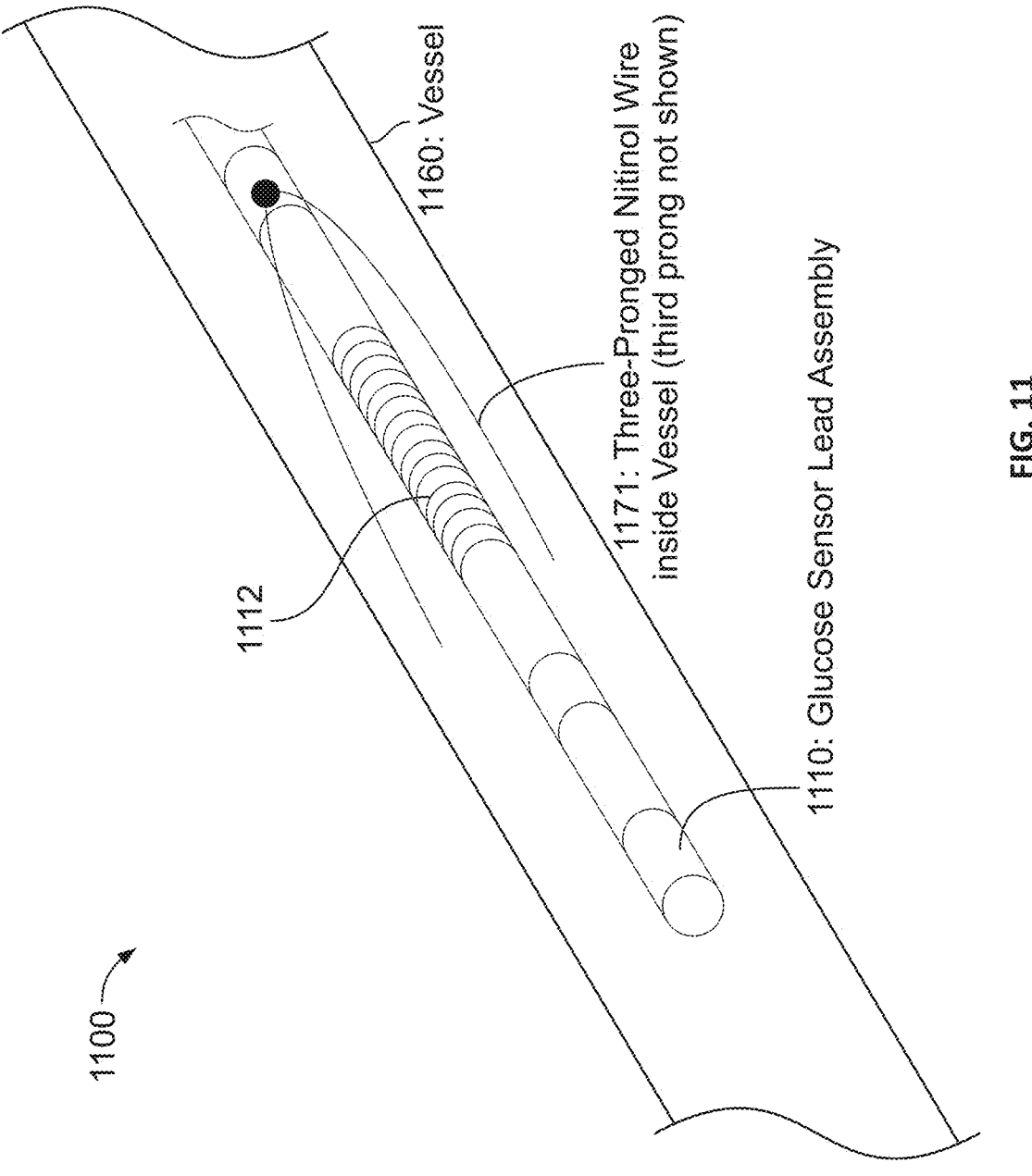
FIG. 11 illustrates an embodiment of a glucose sensor lead assembly comprising an elongated pronged shape-memory element and positioned inside a lumen of a blood vessel, in accordance with some embodiments of the present specification.

FIG. 11 illustrates an embodiment 1100 of a glucose sensor lead assembly 1110 positioned inside lumen of a blood vessel 1160 and comprising an elongated pronged shape-memory element 1171, in accordance with some embodiments of the present specification. Element 1171 is positioned on a proximal side of working electrode 1112, originating from within the body of lead assembly 1110. Each prong of element 1171 protrudes outwards and curves to extend along the linear length of lead assembly 1110 to a distance that is sufficient to cover the complete length of working electrode 1112. In embodiments, a length of each prong is equal and ranges from 0.5 mm to 10 mm. While the figure shows a three-pronged shape-memory element 1171, in alternative embodiments, the number of prongs may differ. In some embodiments, multiple elongated pronged shape-memory elements are configured with the lead assembly, wherein each element is positioned to protect each electrode among multiple electrodes.

Embodiments of the glucose sensor may use a working electrode (312, 712) surface area in a range of 1 mm$^2$ to 1000 mm$^2$, preferably at least 10 mm$^2$ and more preferably around 20 mm$^2$. Increasing the sensor size of a subcutaneously implantable sensor adds overall size in terms of volume and mass. The increase in size is conventionally not desired because they work against the delicate sensor-tissue interface while trying to minimize the foreign body response. Moreover, even if this were not an issue, the sensor-tissue interface in the subcutaneous space is heterogeneous both acutely (due to changes in posture and local oxygen concentration) and chronically (due to angiogenesis integrated with the sensor surface). More specifically, the glucose and oxygen flux per square area are not uniform due to patient posture and the foreign body response. Therefore, a larger surface area of working electrode and/or lead assembly is desirable to accomplish the objective of accurately sensing glucose parameters. These issues are overcome by placing the glucose sensor in the venous vasculature as described in accordance with the present specification. In an embodiment, a proximal coil (counter electrode 316, 716) with a surface area of 150 mm$^2$ is employed. Moreover, the sensor-blood interface is relatively homogenous, providing a consistent amount of glucose flux per mm$^2$. This is further ensured by the positioning element that prevents the working electrode (312, 712) from touching the vessel wall which would occlude glucose and oxygen diffusion to that region.

In another embodiment, to increase glucose oxidase overloading, a thickness of the enzyme layer in the lead assembly is increased. The glucose oxidase at/near the blood-contacting surface of the enzyme membrane layer is the first to become inactivated. When this occurs, glucose needs to travel past this layer(s) of inactivated enzymes to get to active enzymes. The increased diffusion time can result in additional 5, 10, even 30-minute delays in the measurement of blood glucose by the sensor. Any form of delay can be critical for a patient since the high and low glucose level alarms need to be properly times so as to adjust insulin dosing and/or carbohydrate intake accordingly. By having a larger surface area of lead assembly components, as described herein, more glucose oxidase enzyme can be employed while maintaining the thickness of the enzyme layer thin enough so as not to significantly increase diffusion times beyond clinically acceptable levels for proper insulin control and carbohydrate intake. In some embodiments, the enzyme layer is less than 100 microns thick.

Additionally, a ratio of glucose to oxygen must be maintained during glucose monitoring, such that glucose becomes the limiting species in the reaction with the enzyme converting one glucose molecule with one oxygen molecule into gluconic acid and hydrogen peroxide. By increasing surface area, as described above, the oxygen-to-glucose permeability ratio can be further decreased in inversely linear proportion to the surface area increase, thereby maintaining the same amperometric response. The benefit of doing so is the reduction of H$_2$O$_2$ byproduct, which has been shown to deactivate glucose. Minimized H$_2$O$_2$ byproduct, therefore, has a direct benefit on the longevity of the sensor. In some embodiments, a membrane covering the electrodes of the lead assembly has a homogenous enzyme distribution throughout the membrane surface over the working electrode. In some embodiments, the thickness of the cross-linked enzyme layer is such that diffusion to active enzymes (past surface-level inactive enzymes) does not increase overall diffusion time by more than 15 minutes, preferably by no more than 5 minutes. In some embodiments, the surface area of the electrodes is sufficient to have enough enzyme, balanced with enough measurable current, to last at least 2 years in vivo. In some embodiments, the membrane incorporates the enzyme catalase to consume H$_2$O$_2$. In some embodiment, the glucose monitoring device comprises a ketone and/or pH sensor to sense, monitor, or alarm for diabetic ketoacidosis (DKA).

In some embodiments, the glucose monitoring device comprises multiple working electrodes with glucose oxidase membranes, but with a bioresorbable coating that protects the glucose oxidase from blood contact for a pre-defined period of time resulting in preventing the enzyme from decaying due to exposure to blood (any fluid exposure begins the decay process). In such an embodiment, one working electrode may not have this covering and a second working electrode would be designed to decay after 12 months. The duration of protection can be selected such that the uncovered working electrode would still have overloaded glucose oxidase for a sufficiently long period of time (for example, 3 months) to enable it to be a comparison reference for assessing when the bioresorbable membrane has completely degraded from the second working electrode. In another embodiment, the patient returns to the physician office to have the physician switch the device from one working electrode to another. The physician can recalibrate the sensor at that time, if needed.

In embodiments, a microprocessor is programmed to begin measuring the glucose sensor output in advance of the decay (for example, 1 month prior) and compare the second working electrode output to the first working electrode output. Once the output of the two electrodes are considered equivalent by a metric, then the first working electrode is permanently ignored and the second working electrode is the working electrode providing the glucose measurement. In one embodiment, the metric can be that measured current from the two electrodes is within 10% of each other. This approach can be repeated for multiple (more than two) working electrodes. In some embodiments, a multiplexer is configured between the multiple working electrodes to be measured by the potentiostat. In some embodiment, two potentiostats and a multiplexer are used to prevent noise introduced by the signal multiplexing operation, where the noise could compromise glucose measurement accuracy. In such embodiments, the potentiostats remain on the active working electrode and the next active working electrode until the algorithm determines that the permanent use of the next active working electrode is ready. At this point when the next active working electrode is determined to be ready, the previous active working electrode is disabled, the next active working electrode becomes the active working electrode, and the next unused working electrode becomes the next active working electrode in sequence. This is accomplished by making a one-time switch of the working electrodes connections to the potentiostats via the multiplexer. Some embodiments do not use the multiplexer, but include a dedicated potentiostat per working electrode.

The above examples are merely illustrative of the many applications of the system of present specification. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

What is claimed is:

1. A device for continuously monitoring glucose levels in a patient, comprising:

an electronics assembly configured to be positioned outside a fluid-filled lumen of the patient;

a lead assembly in electrical communication with, and physically coupled to, the electronics assembly, wherein the lead assembly is configured to be positioned within the fluid-filled lumen of the patient, the lead assembly comprising:

a lead wire defined by a length and a circumference;

a working electrode, a reference electrode, and a counter electrode disposed on the lead wire, wherein the working electrode encircles the circumference of the lead wire; and a potentiostat positioned within the electronics assembly and configured to control a voltage between the working electrode and the reference electrode, wherein the working electrode, the reference electrode, and the counter electrode collectively form an enzymatic glucose sensor that is structurally configured to maintain electrochemical glucose sensing functionality within the fluid-filled lumen for a continuous implantation period of at least 12 months.

2. The device of claim 1, wherein a combined surface area of the reference electrode and the counter electrode is at least 1.5 times greater than a surface area of the working electrode.

3. The device of claim 1, wherein a surface area of the working electrode is at least 10 mm$^2$.

4. The device of claim 1, wherein the length of the lead wire is between 1 centimeter and 20 centimeters.

5. The device of claim 1, wherein the fluid-filled lumen comprises a central venous vasculature, a peripheral venous vasculature, or a spinal column.

6. The device of claim 1, wherein a structure of at least one of the working electrode, the counter electrode, and the reference electrode comprises one or more of a coil, a ring, and a paddle.

7. The device of claim 1, wherein at least one of the working electrode, the counter electrode, and the reference electrode comprises one or more of platinum, silver-silver chloride, and iridium oxide.

8. The device of claim 1, wherein the reference electrode comprises one or more of platinum, iridium, and a noble metal alloy.

9. The device of claim 1, wherein at least one of the working electrode, the counter electrode, and the reference electrode comprises one or more bioresorbable membranes.

10. The device of claim 1, wherein the electronics assembly comprises an analog to digital converter, a power source, a digital communication circuit, and a microcontroller.

11. The device of claim 1, wherein the electronics assembly is configured to interface wirelessly with an external computing device.

12. A method for continuously monitoring, in-vivo, glucose levels in a patient, comprising:

positioning, within a fluid-filled lumen of the patient, a lead assembly comprising a lead wire having a distal end and a proximal end and defined by a length and a circumference and a working electrode, a reference electrode, and a counter electrode disposed on the lead wire, wherein the working electrode encircles the circumference of the lead wire and wherein the electrodes collectively form an enzymatic glucose sensor; and delivering a voltage bias to the working electrode and the reference electrode using a potentiostat that is part of an electronics assembly physically attached to the lead assembly and positioned outside the fluid-filled lumen of the patient; and maintaining enzymatic electrochemical glucose sensing by the electrodes within the fluid-filled lumen over a continuous implantation period of at least 12 months as a result of the structural configuration of the enzymatic glucose sensor.

13. The device of claim 12, wherein the length of the lead wire is between 1 centimeter and 20 centimeters.

14. The method of claim 12, wherein the fluid-filled lumen comprises a central venous vasculature, a peripheral venous vasculature, or a spinal column.

15. The method of claim 12, wherein a combined surface area of the reference electrode and the counter electrode is at least 1.5 times greater than a surface area of the working electrode.

16. The method of claim 12, wherein a structure of at least one of the working electrode, the counter electrode, and the reference electrode comprises one or more of a coil, a ring, and a paddle.

17. The method of claim 12, wherein at least one of the working electrode, the counter electrode, and the reference electrode comprises one or more of platinum, silver-silver chloride, and iridium oxide.

18. The device of claim 12, wherein the reference electrode comprises one or more of platinum, iridium, and a noble metal alloy.

19. The method of claim 12, wherein at least one of the working electrode, the counter electrode, and the reference electrode comprises one or more bioresorbable membranes.

20. The method of claim 12, wherein the electronics assembly comprises an analog to digital converter, a power source, a digital communication circuit, and a microcontroller.

21. The method of claim 12, wherein the electronics assembly is configured to interface wirelessly with an external computing device.

* * * * *